United States Patent [19]

Sidhu et al.

[11] 4,278,748

[45] Jul. 14, 1981

[54] ABSORBED HYDRAZIDE NUCLEATING AGENTS AND PHOTOGRAPHIC ELEMENTS CONTAINING SUCH AGENTS

[75] Inventors: Jasbir Sidhu, Harrow; Michael J. Simons, Ruislip; Miroslav V. Mijovic, Watford, all of England

[73] Assignee: Eastman Kodak Company, Rochester, N.Y.

[21] Appl. No.: 60,549

[22] Filed: Jul. 25, 1979

[51] Int. Cl.³ .................. G03C 1/40; G03C 5/24; G03C 7/00; G03C 1/06
[52] U.S. Cl. .................. 430/212; 430/217; 430/219; 430/236; 430/598; 430/599; 430/604; 430/410; 548/261
[58] Field of Search ............... 430/598, 599, 604, 410, 430/212, 217, 236, 219; 548/261

[56] References Cited

U.S. PATENT DOCUMENTS

| 4,030,925 | 6/1977 | Leone et al. | 430/598 |
| 4,080,207 | 3/1978 | Leone et al. | 430/598 |

OTHER PUBLICATIONS

J. Sidhu, M. J. Simons, B. D. Baigrie, M. V. Mijovic and D. T. Southby: Research Disclosure, 12-1978, pp. 56-60.

*Primary Examiner*—Won H. Louie, Jr.
*Attorney, Agent, or Firm*—J. Jeffrey Hawley

[57] ABSTRACT

Novel triazole-substituted phenylhydrazide nucleating agents are disclosed as well as silver halide photographic emulsions and elements containing silver halide grains capable of forming an internal latent image having the nucleating agents adsorbed to the surface of the silver halide grains.

17 Claims, No Drawings

ABSORBED HYDRAZIDE NUCLEATING AGENTS AND PHOTOGRAPHIC ELEMENTS CONTAINING SUCH AGENTS

FIELD OF THE INVENTION

The present invention is directed to novel photographic emulsions and elements and to novel adsorbed arylhydrazide nucleating agents. More specifically, this invention is directed to novel adsorbed arylhydrazide nucleating agents and to photographic emulsions and elements containing such nucleating agents in combination with silver halide grains capable of forming an internal latent image.

BACKGROUND OF THE INVENTION

Photographic elements which produce images having an optical density directly related to the radiation received on exposure are said to be negative-working. A positive photographic image can be formed by producing a negative photographic image and then forming a second photographic image which is a negative of the first negative—that is, a positive image. A direct-positive image is understood in photography to be a positive image that is formed without first forming a negative image. Positive dye images which are not direct-positive images are commonly produced in color photography by reversal processing in which a negative silver image is formed and a complementary positive dye image is then formed in the same photographic element. The term "direct reversal" has been applied to direct-positive photographic elements and processing which produces a positive dye image without forming a negative silver image. Direct-positive photography in general and direct reversal photography in particular are advantageous in providing a more straight-forward approach to obtaining positive photographic images.

A conventional approach to forming direct-positive images is to use photographic elements employing internal latent image-forming silver halide grains. After imagewise exposure, the silver halide grains are developed with a surface developer—that is, one which will leave the latent image sites within the silver halide grains substantially unrevealed. Simultaneously, either by uniform light exposure or by the use of a nucleating agent, the silver halide grains are subjected to development conditions that would cause fogging of a negative-working photographic element. The internal latent image-forming silver halide grains which received actinic radiation during imagewise exposure develop under these conditions at a comparatively slow rate, as compared to the internal latent image-forming silver halide grains not imagewise exposed. The result is a direct-positive silver image. In color photography, the oxidized developer that is produced during silver development is used to produce a corresponding positive, direct reversal dye image. Multicolor direct reversal photographic images have been extensively investigated in connection with image-transfer photography.

It has been found advantageous to employ nucleating agents in preference to uniform light exposure in the process described above. The term "nucleating agent" is employed herein in its art-recognized usage to mean a fogging agent capable of permitting the selective development of internal latent image-forming silver halide grains which have not been imagewise exposed in preference to the development of silver halide grains having an internal latent image formed by imagewise exposure.

A favored class of nucleating agents is arylhydrazides. These nucleating agents can be incorporated in a developer solution or directly within a photographic element. Significant advantages have been realized by adsorbing arylhydrazide nucleating agents to the surface of internal latent image-forming silver halide grains. This permits small amounts of the nucleating agents to be employed, as compared with those which are non-adsorbed. However, this narrows the choice of arylhydrazide nucleating agents to those including an adsorption-promoting moiety.

Highly effective adsorbed arylhydrazide nucleating agents are the N-(acylhydrazinophenyl)thioamides of Leone et al, U.S. Pat. No. 4,080,207, and the acylhydrazinophenylthioureas of Leone et al, U.S. Pat. No. 4,030,925. In both of these patents, the nucleating agents incorporate a moiety containing a thiocarbonyl group for promoting the adsorption of the arylhydrazide to the silver halide grain surfaces.

SUMMARY OF THE INVENTION

This invention has as its purpose to provide a novel and highly effective class of adsorbed arylhydrazide nucleating agents. It is a more specific purpose of this invention to provide photographic silver halide emulsions and elements containing these novel adsorbed arylhydrazide nucleating agents. The invention permits a broader choice of adsorbed arylhydrazide nucleating agents useful in low concentrations in photographic silver halide emulsions and elements. The invention also permits photographic processing at reduced pH levels while sustaining nucleating activity.

This invention is directed to triazole-substituted arylhydrazide nucleating agents, silver halide emulsions containing such nucleating agents and silver halide photographic elements containing at least one silver halide emulsion layer containing such nucleating agents.

In one specific aspect, this invention is directed to a silver halide emulsion comprised of silver halide grains capable of forming an internal latent image and, adsorbed to the surface of the silver halide grains, a nucleating amount of a triazole-substituted phenylhydrazide.

In another aspect, this invention is directed to a photographic element comprised of a support and, coated on the support, a silver halide emulsion layer comprising silver halide grains capable of forming an internal latent image and, adsorbed to the surface of said silver halide grains, a nucleating amount of a triazole-substituted phenylhydrazide.

In still another aspect, this invention is directed to a process of obtaining a direct-positive image comprising imagewise exposing a photographic element according to this invention and selectively developing the silver halide grains remaining unexposed.

Preferred triazole-substituted phenylhydrazide nucleating agents are those of the formula:

wherein:
R is an acyl group;
φ is a phenylene or substituted phenylene group; and
A is a moiety comprising of a triazole nucleus capable of promoting adsorption to a silver halide grain surface.

More specifically preferred triazole-substituted phenylhydrazide nucleating agents are those of the formula:

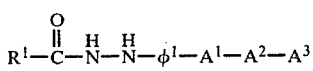

wherein:
$R^1$ is hydrogen, an alkyl, cycloalkyl, haloalkyl, alkoxyalkyl or phenylalkyl substituent or a phenyl nucleus having a Hammett sigma-value-derived electron withdrawing characteristic more positive than $-0.3$;
$\phi^1$ is a m- or p-phenylene or an alkyl-, halo-, benzoxy- or alkoxy-substituted m- or p-phenylene group;
$A^1$ is alkylene or oxyalkylene;

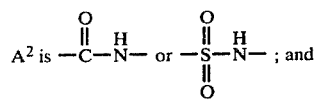

$A^3$ is a triazolyl or benzotriazolyl nucleus;
the alkyl and alkylene moieties in each instance including from 1 to 6 carbon atoms.

Still more specifically preferred triazole-substituted phenylhydrazide nucleating agents are those of the formula:

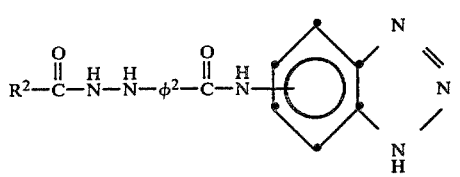

wherein:
$R^2$ is hydrogen or methyl;

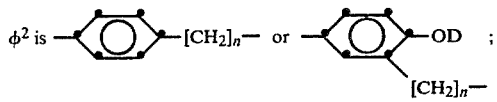

n is an integer of 1 to 4; and
D is alkyl of from 1 to 4 carbon atoms.

DESCRIPTION OF THE PREFERRED EMBODIMENTS

As indicated by R in formula (I), preferred triazole-substituted arylhydrazides employed in the practice of this invention contain an acyl group. From $R^1$ in formula (II), it is apparent that the acyl group is preferably the residue of a carboxylic acid, such as one of the acyclic carboxylic acids, including formic acid, acetic acid, propionic acid, butyric acid, higher homologues of these acids having up to about 7 carbon atoms, and halogen, alkoxy, phenyl and equivalent substituted derivatives thereof. In a preferred form, the acyl group is formed by an unsubstituted acyclic aliphatic carboxylic acid having from 1 to 5 carbon atoms. From $R^2$ in formula (III), it is apparent that specifically preferred acyl groups are formyl and acetyl groups. The alkyl moieties in the substituents to the carboxylic acids are contemplated to have from 1 to 6 carbon atoms, preferably from 1 to 4 carbon atoms.

In addition to the acyclic aliphatic carboxylic acids, it is recognized that the carboxylic acid can be chosen so that $R^1$ is a cyclic aliphatic group having from about 3 to 10 carbon atoms, such as cyclopropyl, cyclobutyl, cyclopentyl, cyclohexyl, methylcyclohexyl, cyclooctyl, cyclodecyl and bridged ring variations, such as bornyl and isobornyl groups. Cyclohexyl is a specifically preferred cycloalkyl substituent. The use of alkoxy, cyano, halogen and equivalent substituted cycloalkyl substituents is contemplated.

In still another form, $R^1$ can be the residue of an aromatic carboxylic acid, such as benzoic acid and substituted derivatives thereof. $R^1$ can take the form of a phenyl nucleus which is either electron donating (electropositive) or electron withdrawing (electronegative); however, phenyl nuclei which are highly electron donating may produce inferior nucleating agents. The electron withdrawing or electron donating characteristic of a specific phenyl nucleus can be assessed by reference to Hammett sigma values. The phenyl nucleus can be assigned a Hammett sigma-value-derived electron withdrawing characteristic which is the algebraic sum of the Hammett sigma values of its substituents (i.e., those of the substituents, if any, to the phenyl group). For example, the Hammett sigma values of any substituents to the phenyl ring of the phenyl nucleus can be determined algebraically simply by determining from the literature the known Hammett sigma values for each substituent and obtaining the algebraic sum thereof. Electron withdrawing substituents are assigned positive sigma values, while electron donating substituents are assigned negative sigma values. In a preferred form, $R^1$ is a phenyl nucleus having a Hammett sigma-value-derived electron withdrawing characteristic more positive than $-0.3$.

Exemplary meta and para sigma values and procedures for their determination are set forth by J. Hine in *Physical Organic Chemistry*, second edition, page 87, published in 1962; H. VanBekkum, P. E. Verkade and B. M. Wepster in *Rec. Trav. Chim.*, Volume 78, page 815, published in 1959; P. R. Wells in *Chem. Revs.*, Volume 63, page 171, published in 1963; by H. H. Jaffe in *Chem. Revs.*, Volume 53, page 191, published in 1953; by M. J. S. Dewar and P. J. Grisdale in *J. Amer. Chem. Soc.*, Volume 84, page 3548, published in 1962; and by Barlin and Perrin in *Quart. Revs.*, Volume 20, page 75 et seq, published in 1966. For the purposes of this invention, ortho substituents to the phenyl ring can be assigned to the published para sigma values.

In a preferred form, $R^1$ can be the residue of an aromatic carboxylic acid, such as benzoic acid; alkyl, halo-, cyano or alkoxy-substituted benzoic acid or an equivalent thereof. Where $R^1$ is the residue of a substituted benzoic acid, it is preferred that the benzoic acid be para or 4-ring position substituted. The alkyl moieties of the ring substituents preferably have from 1 to 6 carbon atoms. Fluoro, chloro, bromo and iodo halogen ring substituents are specifically contemplated.

As indicated by $\phi$ in formula (I), preferred triazole-substituted arylhydrazides employed in the practice of this invention contain a phenylene or substituted phenylene group. As indicated by $\phi^1$ in formula (II), specifically preferred phenylene groups are m- and p-phenylene groups. Exemplary of preferred phenylene substituents are alkoxy substituents having from 1 to 6 carbon atoms, alkyl substituents having from 1 to 6 carbon atoms, fluoro-, chloro-, bromo- and iodo-substituents. Unsubstituted p-phenylene groups and m-phenylene groups which are substituted in the 4-ring position (with respect to the hydrazide) with an alkoxy group are specifically preferred. Specifically preferred alkyl moieties are those which have from 1 to 4 carbon atoms. While phenylene and substituted phenylene groups are preferred linking groups, other functionally equivalent divalent aryl groups, such as naphthalene groups, can be employed.

Attached to the phenylene or other divalent aryl linking group is a moiety, identified as A in formula (I), capable of promoting adsorption of the nucleating agent to a silver halide grain surface. To promote adsorption, the moiety is comprised of a triazole nucleus. The triazole nucleus can consist of a 1,2,3-triazole ring or a 1,2,4-triazole ring. The 1,2,3-triazole ring can be fused with a benzene ring to form a benzotriazole ring. The triazole nucleus can be attached to the arylhydrazide moiety in the form of a 1,2,3-triazol-4-yl, 1,2,4-triazol-3-yl, benzotriazol-5-yl or benzotriazol-4-yl moiety. Substituents to the ring carbon atoms, such as those described in connection with $\phi^1$, are contemplated. It is believed that the triazole nucleus promotes adsorption to silver halide grain surfaces by reason of containing an ionizable hydrogen attached to the 1-ring position nitrogen. A tetrazolyl nucleus exhibits the same characteristic and can, if desired, be substituted for the triazolyl nucleus.

The moiety A, which promotes adsorption to silver halide grain surfaces, can be comprised of, in addition to the triazole nucleus, a divalent linking group. The function of the divalent linking group is to attach the triazolyl nucleus, which is active as an adsorption promoting moiety, to the arylhydrazide group, which is the active nucleating moiety. The divalent linking group can be the product of any synthetically convenient approach to joining the arylhydrazide and triazolyl groups.

The triazole-substituted arylhydrazide nucleating agents of this invention can be prepared by procedures which are, in themselves, of a type well known in the art. For example, a p-aminophenylcarboxylic acid can be diazotized and the resulting diazo compound reduced with stannous chloride or a similar reducing agent to form the corresponding hydrazine. The hydrazine can be converted to a hydrazide by reaction with a carboxylic acid. This results in a p-acylhydrazino-phenylcarboxylic acid which can be reacted with an amino or hydroxy triazole or benzotriazole ring carbon atom substituent to form the desired triazolyl-p-phenylenehydrazide.

A preferred synthetic approach to forming the triazole-substituted arylhydrazide nucleating agents of this invention when the linking group contains an amido or ester group is to employ a p-acylhydrazinophenylcarboxylic acid or p-acylhydrazinophenoxycarboxylic acid as a starting material. Alternatively, the acylhydrazino substituent can conveniently be meta to the carboxylic acid when the phenyl ring position para to the carboxylic acid is occupied by a substituent, such as an oxy substituent—e.g., an alkoxy (preferably methoxy) or benzyloxy substituent. An hydroxy or amine substituted triazole or benzotriazole, in which an hydroxy group or a primary or secondary amine group is linked to a ring carbon atom directly or indirectly through an alkylene group, is reacted with the carboxylic acid by forming an active ester of the carboxylic acid with 1-hydroxybenzotriazole in the presence of dicyclocarbodiimide and then forming the amide or ester via nucleophilic substitution of the 1-hydroxybenzotriazole with the hydroxy or amine-substituted triazole or benzotriazole. In one specific approach, the carboxylic acid is reacted with the 1-hydroxybenzotriazole in the presence of dicyclohexylcarbodiimide at 0° C., and the active ester which is formed as an intermediate is then reacted with the hydroxy or amine-substituted triazole or benzotriazole at temperatures above the ambient. In a variant form, all of the reactants can be mixed at a temperature of 0° C. and the reaction completed at an elevated temperature.

The triazole-substituted arylhydrazide nucleating agents of this invention can also contain in the divalent linking group a sulfonamido group. For example, instead of employing an hydroxy or amine-substituted triazole or benzotriazole as described above, a corresponding chlorosulfonyl-substituted triazole or benzotriazole can be employed. The chlorosulfonyl-substituted triazole or benzotriazole is reacted with an amino-substituted nitrobenzene. Thereafter, the nitro group can be converted to a hydrazido group by the diazotization and reduction procedures described above.

In the preferred triazole-substituted phenylhydrazide nucleating agents of this invention, it is apparent from the foregoing discussion of preferred and exemplary syntheses that the triazolyl or benzotriazolyl adsorption promoting moiety is preferably joined to the phenylhydrazide nucleating moiety through a divalent linking group which takes the form of an alkylene moiety attached to the phenyl ring of the phenylhydrazide directly or through an oxy linkage, as indicated by $A^1$ in formula (II). The alkylene moiety can contain from 1 to 6 carbon atoms, and in a specifically preferred form indicated in formula (III), wherein $\phi^2$ is a phenylenealkylene group, the alkylene moiety consists of from 1 to 4 methylene groups. As indicated by $\phi^1$ in formula (II), the phenylene moiety can be substituted, such as with a halo-, alkyl, benzyloxy or alkoxy substituent, wherein the alkyl moieties thereof contain from 1 to 6 carbon atoms. When the alkylene moiety occupies a position meta to the acylhydrazino group attached to the phenyl ring, a para position phenyl ring substituent is also preferably present. As indicated by $\phi^2$ in formula (III), an alkoxy substituent having from 1 to 4 carbon atoms, most preferably a methoxy substituent, occupies the para phenyl ring position when the alkylene moiety is meta to the acylhydrazino group.

As indicated by $A^2$ in formula (II), the alkylene moiety is preferably linked to the triazolyl or benzotriazolyl nucleus by a

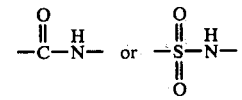

divalent group. The alkylene moiety is linked to the triazolyl or benzotriazolyl nucleus through an amido group when the alkylene moiety and the carbonyl portion of the amido group are the residue of a carboxylic acid attached to the phenyl ring of the phenylenehydrazide moiety. Alternatively, the alkylene moiety can be attached to the triazole or benzotriazole nucleus through a sulfamoyl group when the sulfo portion of the sulfamoyl group is the residue of the sulfonylchloride substituent to the triazole or benzotriazole employed in synthesis.

Specific preferred triazole-substituted arylhydrazide nucleating agents are disclosed below in the examples.

The triazole-substituted arylhydrazide nucleating agents can be employed with any conventional photographic element capable of forming a direct positive image containing coated on a photographic support at least one silver halide emulsion layer containing a vehicle and silver halide grains capable of forming an internal latent image upon exposure to actinic radiation. As employed herein, the terms "internal latent image silver halide grains" and "silver halide grains capable of forming an internal latent image" are employed in the art-recognized sense of designating silver halide grains which produce substantially higher optical densities when coated, imagewise exposed and developed in an internal developer than when comparably coated, exposed and developed in a surface developer. Preferred internal latent image silver halide grains are those which, when examined according to normal photographic testing techniques, by coating a test portion on a photographic support at a density of from 3 to 4 grams per square meter, exposing to a light intensity scale (such as, for example, with a 500-watt tungsten lamp at a distance of 61 cm) for a fixed time between $1 \times 10^{-2}$ and 1 second and developing for 5 minutes at 25° C. in Kodak Developer DK-50 (a surface developer), provide a density of at least 0.5 less than when this testing procedure is repeated, substituting for the surface developer Kodak Developer DK-50 containing 0.5 gram per liter of potassium iodide (an internal developer). The internal latent image silver halide grains most preferred for use in the practice of this invention are those which, when tested using an internal developer and a surface developer as indicated above, produce an optical density with the internal developer at least 5 times that produced by the surface developer. It is additionally preferred that the internal latent image silver halide grains produce an optical density of less than 0.4 and, most preferably, less than 0.25 when coated, exposed and developed in surface developer as indicated above—that is, the silver halide grains are initially substantially unfogged and free of latent image on their surface.

The surface developer referred to herein as Kodak Developer DK-50 is described in the *Handbook of Chemistry and Physics*, 30th edition, 1947, Chemical Rubber Publishing Company, Cleveland, Ohio, page 2558, and has the following composition:

| | |
|---|---|
| Water, about 125° F. (52° C.) | 500.0 cc |
| N-methyl-p-aminophenol sulfate | 2.5 g |
| Sodium sulfite, desiccated | 30.0 g |
| Hydroquinone | 2.5 g |
| Sodium metaborate | 10.0 g |
| Potassium bromide | 0.5 g |
| Water to make | 1.0 liter |

Internal latent image silver halide grains which can be employed in the practice of this invention are well known in the art. Patents teaching the use of internal latent image silver halide grains in photographic emulsions and elements include Davey et al, U.S. Pat. No. 2,592,250, issued May 8, 1952; Porter et al, U.S. Pat. No. 3,206,313, issued Sept. 14, 1965; Milton, U.S. Pat. No. 3,761,266, issued Sept. 25, 1973; Ridgway, U.S. Pat. No. 3,586,505, issued June 22, 1971; Gilman et al, U.S. Pat. No. 3,772,030, issued Nov. 13, 1973; Gilman et al, U.S. Pat. No. 3,761,267, issued Sept. 25, 1973; and Evans, U.S. Pat. No. 3,761,276, issued Sept. 25, 1973, the disclosures of which are hereby incorporated by reference.

The internal latent image silver halide grains preferably contain bromide as the predominant halide. The silver bromide grains can consist essentially of silver bromide or can contain silver bromoiodide, silver chlorobromide, silver chlorobromoiodide crystals and mixtures thereof. Internal latent image-forming sites can be incorporated into the grains by either physical or chemical internal sensitization. Davey et al, cited above, for example, teaches the physical formation of internal latent image-forming sites by the halide conversion technique. Chemical formation of internal latent image-forming sites can be produced through the use of sulfur, gold, selenium, tellurium and/or reduction sensitizers of the type described, for example, in Sheppard et al, U.S. Pat. No. 1,623,499, issued Apr. 5, 1927; Waller et al, U.S. Pat. No. 2,399,083, issued Apr. 23, 1946; McVeigh, U.S. Pat. No. 3,297,447, issued Jan. 10, 1967 and Dunn, U.S. Pat. No. 3,297,446, issued Jan. 10, 1967, as taught in the patents cited in the preceding paragraph. Internal latent image sites can also be formed through the incorporation of metal dopants, particularly Group VIII noble metals, such as ruthenium, rhodium, palladium, iridium, osmium and platinum, as taught by Berriman, U.S. Pat. No. 3,367,778, issued Feb. 6, 1968. The preferred foreign metal ions are polyvalent metal ions which include the above-noted Group VIII dopants, as well as polyvalent metal ions such as lead, antimony, bismuth, arsenic and the like. In highly preferred embodiments, the silver halide grains are formed in the presence of bismuth, lead or iridium ions. In a preferred approach, the internal latent image sites can be formed within the silver halide grains during precipitation of silver halide. In an alternate approach, a core grain can be formed which is treated to form the internal image sites and then a shell deposited over the core grains, as taught by Porter et al, cited above.

The silver halide grains employed in the practice of this invention are preferably monodispersed, and in some embodiments are preferably large-grain emulsions made according to Wilgus, German OLS No. 2,107,118, published Sept. 2, 1971, which is incorporated herein by reference. The monodispersed emulsions are those which comprise silver halide grains having a substantially uniform diameter. Generally, in such emulsions, no more than about 5 percent by number of the silver halide grains smaller than the mean grain size and/or no more than about 5 percent by weight of the silver halide grains larger than the mean grain size vary in diameter from the mean grain diameter by more than about 40 percent. Preferred photographic emulsions of this invention comprise silver halide grains, at least 95 percent by weight of said grains having a diameter which is within 40 percent and preferably within about 30 percent of the mean grain diameter. Mean grain diameter, i.e., average grain size, can be determined using conventional methods, e.g., such as projective area, as shown in an article by Trivelli and Smith entitled "Empirical Relations Between Sensitometric and Size-Frequency Characteristics in Photographic Emulsion Series" in *The Photographic Journal*, Volume LXXIX, 1939, pages 330 through 338. The aforementioned uniform size distribution of silver halide grains is a characteristic of the grains in monodispersed photographic silver halide emulsions. Silver halide grains having a narrow size distribution can be obtained by controlling the conditions at which the silver halide grains are prepared using a double run procedure. In such a procedure, the silver halide grains are prepared by simultaneously running an aqueous solution of a silver salt, such as silver nitrate, and an aqueous solution of a water-soluble halide, for example, an alkali metal halide such as potassium bromide, into a rapidly agitated aqueous solution of a silver halide peptizer, preferably gelatin, a gelatin derivative or some other protein peptizer. Suitable methods for preparing photographic silver halide emulsions having the required uniform particle size are disclosed in an article entitled "Ia: Properties of Photographic Emulsion Grains", by Klein and Moisar, *The Journal of Photographic Science*, Volume 12, 1964, pages 242 through 251; an article entitled "The Spectral Sensitization of Silver Bromide Emulsions on Different Crystallographic Faces", by Markocki, *The Journal of Photographic Science*, Volume 13, 1965, pages 85 through 89; an article entitled "Studies on Silver Bromide Sols, Part I. The Formation and Aging of Monodispersed Silver Bromide Sols", by Ottewill and Woodbridge, *The Journal of Photographic Science*, Volume 13, 1965, pages 98 through 103; and an article entitled "Studies on Silver Bromide Sols, Part II. The Effect of Additives on the Sol Particles", by Ottewill and Woodbridge, *The Journal of Photographic Science*, Volume 13, 1965, pages 104 through 107.

Where internal latent image sites have been formed through internal chemical sensitization or the use of metal dopants, the surface of the silver halide grains can be sensitized to a level below that which will produce substantial density in a surface developer—that is, less than 0.4 when coated, exposed and surface developed as described above. The silver halide grains are preferably predominantly silver bromide grains chemically surface sensitized to a level which would provide a maximum density of at least 0.5 using undoped silver halide grains of the same size and halide composition when coated, exposed and developed as described above.

Surface chemical sensitization can be undertaken using techniques such as those disclosed by Sheppard, Waller et al, McVeigh or Dunn, cited above. The silver halide grains can also be surface sensitized with salts of the noble metals, such as ruthenium, palladium and platinum. Representative compounds are ammonium chloropalladate, potassium chloroplatinate and sodium chloropalladite, which are used for sensitizing in amounts below that which produces any substantial fog inhibition, as described in Smith and Trivelli, U.S. Pat. No. 2,448,060, issued Aug. 31, 1948, and as antifoggants in higher amounts, as described in Trivelli and Smith, U.S. Pat. No. 2,566,245, issued Aug. 28, 1951, and U.S. Pat. No. 2,566,263, issued Aug. 28, 1951. The silver halide grains can also be chemically sensitized with reducing agents, such as stannous salts (Carroll, U.S. Pat. No. 2,487,850, issued Nov. 15, 1949), polyamines, such as diethylene triamine (Lowe et al, U.S. Pat. No. 2,518,698, issued Aug. 15, 1960), polyamines, such as spermine (Lowe et al, U.S. Pat. No. 2,521,925, issued Sept. 12, 1950), or bis($\beta$-aminoethyl)sulfide and its water-soluble salts (Lowe et al, U.S. Pat. No. 2,521,926, issued Sept. 12, 1950).

The photographic silver halide emulsion layers and other layers of the photographic elements can contain various colloids alone or in combination as vehicles. Suitable hydrophilic materials include both naturally-occurring substances such as proteins, protein derivatives, cellulose derivatives—e.g., cellulose esters, gelatin—e.g., alkali-treated gelatin (cattle bone or hide gelatin) or acid-treated gelatin (pigskin gelatin), gelatin derivatives—e.g., acetylated gelatin, phthalated gelatin and the like, polysaccharides such as dextran, gum arabic, zein, casein, pectin, collagen derivatives, collodion, agar-agar, arrowroot, albumin and the like, as described in Yutzy et al, U.S. Pat. Nos. 2,614,928 and '929; Lowe et al, U.S. Pat. Nos. 2,691,582, 2,614,930 and '931, 2,327,808 and 2,448,534; Gates et al, U.S. Pat. Nos. 2,787,545 and 2,956,880; Himmelmann et al, U.S. Pat. No. 3,061,436; Farrell et al, U.S. Pat. No. 2,816,027; Ryan, U.S. Pat. Nos. 3,132,945, 3,138,461 and 3,186,846; Dersch et al, U.K. Pat. No. 1,167,159 and U.S. Pat. Nos. 2,960,405 and 3,436,220; Geary, U.S. Pat. No. 3,486,896; Gazzard, U.K. Pat. No. 793,549; Gates et al, U.S. Pat. Nos. 2,992,213, 3,157,506, 3,184,312 and 3,539,353; Miller et al, U.S. Pat. No. 3,227,571; Boyer et al, U.S. Pat. No. 3,532,502; Malan, U.S. Pat. No. 3,551,151; Lohmer et al, U.S. Pat. No. 4,018,609; Luciani et al, U.K. Pat. No. 1,186,790; U.K. Pat. No. 1,489,080; and Hori et al, Belgian Pat. No. 856,631, U.K. Pat. No. 1,490,644, U.K. Pat. No. 1,483,551; Arase et al, U.K. Pat. No. 1,459,906; Salo, U.S. Pat. Nos. 2,110,491 and 2,311,086; Fallesen, U.S. Pat. No. 2,343,650; Yutzy, U.S. Pat. No. 2,322,085; Lowe, U.S. Pat. No. 2,563,791; Talbot et al, U.S. Pat. No. 2,725,293; Hilborn, U.S. Pat. No. 2,748,022; DePauw et al, U.S. Pat. No. 2,956,883; Ritchie, U.K. Pat. No. 2,095; DeStubner, U.S. Pat. No. 1,752,069; Sheppard et al, U.S. Pat. No. 2,127,573; Lierg, U.S. Pat. No. 2,256,720; Gaspar, U.S. Pat. No. 2,361,936; Farmer, U.K. Pat. No. 15,727; Stevens, U.K. Pat. No. 1,062,116; and Yamamoto et al, U.S. Pat. No. 3,923,517.

Photographic emulsion layers and other layers of photographic elements, such as overcoat layers, interlayers and subbing layers, as well as receiving layers in imagetransfer elements, can also contain alone or in combination with hydrophilic water-permeable colloids as vehicles or vehicle extenders (e.g., in the form of latices), synthetic polymeric peptizers, carriers and/or binders such as poly(vinyl lactams), acrylamide polymers, polyvinyl alcohol and its derivatives, polyvinyl acetals, polymers of alkyl and sulfoalkyl acrylates and methacrylates, hydrolyzed polyvinyl acetates, polyamides, polyvinyl pyridine, acrylic acid polymers, maleic anhydride copolymers, polyalkylene oxides, methacrylamide copolymers, polyvinyl oxazolidinones, maleic acid copolymers, vinylamine copolymers, methacrylic acid copolymers, acryloyloxyalkylsulfonic acid copolymers, sulfoalkylacrylamide copolymers, polyalkyleneimine copolymers, polyamines, N,N-dialkylaminoalkyl acrylates, vinyl imidazole copolymers, vinyl sulfide copolymers, halogenated styrene polymers, amineacrylamide polymers, polypeptides and the like, as described in Hollister et al, U.S. Pat. Nos. 3,679,425, 3,706,564 and 3,813,251; Lowe, U.S. Pat. Nos. 2,253,078, 2,276,322 and '323, 2,281,703, 2,311,058 and 2,414,207; Lowe et al, U.S. Pat. Nos. 2,484,456, 2,541,474 and 2,632,704; Perry et al, U.S. Pat. No. 3,425,836; Smith et al, U.S. Pat. Nos. 3,415,653 and 3,615,624; Smith, U.S. Pat. No. 3,488,708; Whiteley et al, U.S. Pat. Nos. 3,392,025 and 3,511,818; Fitzgerald, U.S. Pat. Nos. 3,681,079, 3,721,565, 3,852,073, 3,861,918 and 3,925,083; Fitzgerald et al, U.S. Pat. No. 3,879,205; Nottorf, U.S. Pat. No. 3,142,568; Houck et al, U.S. Pat. Nos. 3,062,674 and 3,220,844; Dunn et al, U.S. Pat. No. 2,882,161; Schupp, U.S. Pat. No. 2,579,016; Weaver, U.S. Pat. No. 2,829,053; Alles et al, U.S. Pat. No. 2,698,240; Priest et al, U.S. Pat. No. 3,003,879; Merrill et al, U.S. Pat. No. 3,419,397; Stonham, U.S. Pat. No. 3,284,207; Lohmer et al, U.S. Pat. No. 3,167,430; Williams, U.S. Pat. No. 2,957,767; Dawson et al, U.S. Pat. No. 2,893,867; Smith et al, U.S. Pat. Nos. 2,860,986 and 2,904,539; Ponticello et al, U.S. Pat. Nos. 3,929,482 and 3,860,428; Ponticello, U.S. Pat. No. 3,939,130; Dykstra, U.S. Pat. No. 3,411,911; Dykstra et al, Canadian Pat. No. 774,054; Ream et al, U.S. Pat. No. 3,287,289; Smith, U.K. Pat. No. 1,466,600; Stevens, U.K. Pat. No. 1,062,116; Fordyce, U.S. Pat. No. 2,211,323; Martinez, U.S. Pat. No. 2,284,877; Watkins, U.S. Pat. No. 2,420,455; Jones, U.S. Pat. No. 2,533,166; Bolton, U.S. Pat. No. 2,495,918; Graves, U.S. Pat. No. 2,289,775; Yackel, U.S. Pat. No. 2,565,418; Unruh et al, U.S. Pat. Nos. 2,865,893 and 2,875,059; Rees et al, U.S. Pat. No. 3,536,491; Broadhead et al, U.K. Pat. No. 1,348,815; Taylor et al, U.S. Pat. No. 3,479,186; Merrill et al, U.S. Pat. No. 3,520,857; Bacon et al, U.S. Pat. No. 3,690,888; Bowman, U.S. Pat. No. 3,748,143; Dickinson et al, U.K. Pat. Nos. 808,227 and '228; Wood, U.K. Pat. No. 822,192; and Iguchi et al, U.K. Pat. No. 1,398,055.

The layers of the photographic elements can be coated on a variety of supports. Typical photographic supports include polymeric film, wood fiber—e.g., paper, metallic sheet and foil, glass and ceramic supporting elements provided with one or more subbing layers to enhance the adhesive, antistatic, dimensional, abrasive, hardness, frictional, antihalation and/or other properties of the support surface.

Typical of useful polymeric film supports are films of cellulose nitrate and cellulose esters, such as cellulose triacetate and diacetate, polystyrene, polyamides, homo- and co-polymers of vinyl chloride, poly(vinyl acetal), polycarbonate, homo- and co-polymers of olefins, such as polyethylene and polypropylene, and polyesters of dibasic aromatic carboxylic acids with divalent alcohols, such as poly(ethylene terephthalate).

Typical of useful paper supports are those which are partially acetylated or coated with baryta and/or a polyolefin, particularly a polymer of an α-olefin containing 2 to 10 carbon atoms, such as polyethylene, polypropylene, copolymers of ethylene and propylene and the like.

Polyolefins, such as polyethylene, polypropylene and polyallomers—e.g., copolymers of ethylene with propylene, as illustrated by Hagemeyer et al, U.S. Pat. No. 3,478,128, are preferably employed as resin coatings over paper, as illustrated by Crawford et al, U.S. Pat. No. 3,411,908, and Joseph et al, U.S. Pat. No. 3,630,740, over polystyrene and polyester film supports, as illustrated by Crawford et al, U.S. Pat. No. 3,630,742, or can be employed as unitary flexible reflection supports, as illustrated by Venor et al, U.S. Pat. No. 3,973,963.

Preferred cellulose ester supports are cellulose triacetate supports, as illustrated by Fordyce et al, U.S. Pat. Nos. 2,492,977, '978 and 2,739,069, as well as mixed cellulose ester supports, such as cellulose acetate propionate and cellulose acetate butyrate, as illustrated by Fordyce et al, U.S. Pat. No. 2,739,070.

Preferred polyester film supports are comprised of linear polyester, such as illustrated by Alles et al, U.S. Pat. No. 2,627,088; Wellman, U.S. Pat. No. 2,720,503; Alles, U.S. Pat. No. 2,779,684; and Kibler et al, U.S. Pat. No. 2,901,466. Polyester films can be formed by varied techniques, as illustrated by Alles, cited above, Czerkas et al, U.S. Pat. No. 3,663,683 and Williams et al, U.S. Pat. No. 3,504,075, and modified for use as photographic film supports, as illustrated by Van Stappen, U.S. Pat. No. 3,277,576; Nadeau et al, U.S. Pat. No. 3,501,301; Reedy et al, U.S. Pat. No. 3,589,905; Babbitt et al, U.S. Pat. No. 3,850,640; Bailey et al, U.S. Pat. No. 3,888,678; Hunter, U.S. Pat. No. 3,904,420; and Mallinson et al, U.S. Pat. No. 3,928,697.

The photographic elements can employ supports which are resistant to dimensional change at elevated temperatures. Such supports can be comprised of linear condensation polymers which have glass transition temperatures above about 190° C., preferably 220° C., such as polycarbonates, polycarboxylic esters, polyamides, polysulfonamides, polyethers, polyimides, polysulfonates and copolymer variants, as illustrated by Hamb, U.S. Pat. Nos. 3,634,089 and 3,772,405; Hamb et al, U.S. Pat. Nos. 3,725,070 and 3,793,249; Wilson, *Research Disclosure*, Volume 118, February 1974, Item 11833, and Volume 120, April 1974, Item 12046; Conklin et al, *Research Disclosure*, Volume 120, April 1974, Item 12012; *Product Licensing Index*, Volume 92, December 1971, Items 9205 and 9207; *Research Disclosure*, Volume 101, September 1972, Items 10119 and 10148; *Research Disclosure*, Volume 106, February 1973, Item 10613; *Research Disclosure*, Volume 117, January 1974, Item 11709; and *Research Disclosure*, Volume 134, June 1975, Item 13455. Both *Research Disclosure* and *Product Licensing Index* are published by Industrial Opportunities, Ltd., Homewell, Havant, Hampshire, P09 1EF, United Kingdom.

The triazole-substituted arylhydrazide nucleating agents of this invention can be employed in any desired concentration that will permit a degree of selectivity in developing imagewise silver halide grains capable of forming an internal latent image, which grains have not been imagewise exposed, as compared to silver halide grains containing an internal latent image formed by imagewise exposure.

In a preferred form of this invention, the triazole-substituted arylhydrazide nucleating agents are adsorbed to the surface of the internal latent image silver halide grains and employed in concentrations ranging from 0.5 to 500 mg of adsorbed nucleating agent per mole of silver. Preferably, 1 to 100 mg of adsorbed nucleating agent per mole of silver is employed. Optimum concentrations can, of course, vary somewhat from one application to another. Where the triazole-substituted arylhydrazide nucleating agent is to be adsorbed to the surface of the silver halide grains, it can be adsorbed using the procedure well known to those skilled in the art for adsorbing sensitizing dyes, such as cyanine and merocyanine dyes, to the surface of silver halide grains.

A simple exposure and development process can be used to form a direct-positive image. In one embodiment, a photographic element comprising at least one layer of a silver halide emulsion as described above can be imagewise exposed and then developed in a silver halide surface developer.

It is understood that the term "surface developer" encompasses those developers which will reveal the surface latent image on a silver halide grain, but will not reveal substantial internal latent image in an internal image-forming emulsion, and under the conditions generally used develop a surface-sensitive silver halide emulsion. The surface developers can generally utilize any of the silver halide developing agents or reducing agents, but the developing bath or composition is generally substantially free of a silver halide solvent (such as water-soluble thiocyanates, water-soluble thioethers, thiosulfates, ammonia and the like) which will disrupt or dissolve the grain to reveal substantial internal image. Low amounts of excess halide are sometimes desirable in the developer or incorporated in the emulsion as halide-releasing compounds, but high amounts of iodide or iodide-releasing compounds are generally avoided to prevent substantial disruption of the grain.

Typical silver halide developing agents which can be used in the developing compositions of this invention include hydroquinones, catechols, aminophenols, 3-pyrazolidones, ascorbic acid and its derivatives, reductones, phenylenediamines and the like, or combinations thereof. The developing agents can be incorporated in the photographic elements wherein they are brought in contact with the silver halide after imagewise exposure; however, in certain embodiments they are preferably employed in the developing bath.

The developing compositions used in the process of this invention can also contain certain antifoggants and development restrainers, or optionally they can be incorporated in layers of the photographic element. For example, in some applications, improved results can be obtained when the direct positive emulsions are processed in the presence of certain antifoggants, as disclosed in Stauffer U.S. Pat. No. 2,497,917, which is incorporated herein by reference.

Typical useful antifoggants include benzotriazoles, such as benzotriazole, 5-methylbenzotriazole, 5-ethylbenzotriazole and the like, benzimidazoles such as 5-nitrobenzimidazole and the like, benzothiazoles such as 5-nitrobenzothiazole, 5-methylbenzothiazole and the like, heterocyclic thiones such as 1-methyl-2-tetrazoline-5-thione and the like, triazines such as 2,4-dimethylamino-6-chloro-5-triazine and the like, benzoxazoles such as ethylbenzoxazole and the like, and pyrroles such as 2,5-dimethylpyrrole and the like.

In certain embodiments, good results are obtained when the elements are processed in the presence of high levels of the antifoggants mentioned above. When antifoggants such as benzotriazoles are used, good results can be obtained when the processing solution contains up to 5 grams per liter and preferably 1 to 3 grams per liter; when they are incorporated in the photographic element, concentrations of up to 1,000 mg per mole of Ag and preferably concentrations of 100 to 500 mg per mole of Ag are employed.

The essential features of the triazole-substituted arylhydrazide nucleating agents of this invention and the silver halide emulsions and photographic elements in which they are incorporated, as well as procedures for their use and processing, are described above. It is appreciated that, in preferred photographic applications, the emulsions and elements can contain additional features which are in themselves well known to those familiar with the photographic arts. Further, these applications can entail conventional modifications in the procedures described above. A variety of such features are disclosed in *Research Disclosure*, Volume 176, December 1978, Item 17643, the disclosure of which is herein incorporated by reference, particularly Paragraph II, *Emulsion Washing;* Paragraph IV, *Spectral Sensitization and Desensitization;* Paragraph V, *Brighteners;* Paragraph VI, *Antifoggants and Stabilizers;* Paragraph VIII, *Absorbing and Scattering Materials;* Paragraph X, *Hardeners;* Paragraph XI, *Coating Aids;* Paragraph XII, *Plasticizers and Lubricants;* Paragraph XIII, *Antistatic Layers;* Paragraph XIV, *Methods of Addition;* Paragraph XV, *Coating and Drying Procedures;* Paragraph XVI, *Matting Agents;* Paragraph XVIII, *Exposure;* Paragraph XX, *Developing Agents;* and Paragraph XXI, *Development Modifiers.*

The silver halide emulsions can be spectrally sensitized with cyanine, merocyanine, and other polymethine dyes and supersensitizing combinations thereof well known in the art. Spectral sensitizers in conventional surface-sensitive emulsions are comparably effective in the emulsions of this invention. In general, they enhance nucleation. Nonionic, zwitterionic and anionic spectral sensitizers are preferred. Particularly effective are carboxy-substituted merocyanine dyes of the thiohydantoin type described by Stauffer and Spence, U.S. Pat. No. 2,490,758.

Effective red sensitizers are the carbocyanines of Formula (IV):

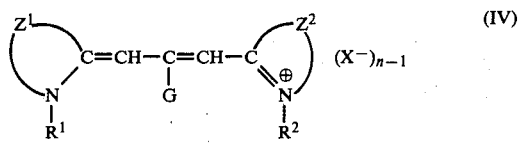

wherein:
each of $Z^1$ and $Z^2$ represents the atoms necessary to form a benzothiazole, benzoselenazole, naphthothiazole or naphthoselenazole, the benzothiazole and benzoselenazole being preferably 5- and/or 6-substituted with groups such as lower alkyl, lower alkoxy, chloro, bromo, fluoro, hydroxy, acylamino, cyano and trifluoromethyl;

G represents hydrogen and lower alkyl, preferably ethyl or methyl;

each of $R^1$ and $R^2$ represents lower alkyl or hydroxy(lower)alkyl, at least one of $R^1$ and $R^2$ being preferably acid-substituted(lower)alkyl, such as carboxyethyl, sulfopropyl, sulfatoethyl, etc;

X represents an acid anion; and n is 1 or 2.

Particularly effective are certain supersensitizing combinations of the above dyes with each other and with dyes or other adsorbed organic compounds having polarographic oxidation potentials ($E_{ox}$) of about 0.3 to 0.9 volt. Many such combinations are described in U.S. Pat. Nos. 2,075,048; 2,313,922; 2,533,426; 2,704,714; 2,704,717; 2,688,545 and 3,672,898, and include, as well, the acid-substituted analogues thereof well known in the art.

Effective green sensitizers are cyanines and merocyanines of Formulas (V) and (VI):

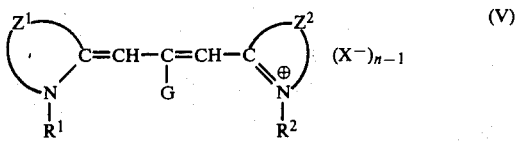

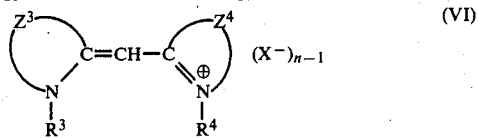

wherein:
each of $Z^1$ and $Z^2$ represents the atoms necessary to form benzoxazole and benzimidazole nuclei, benzimidazole being substituted in the 3-position by lower alkyl or aryl, and preferably in the 5- and/or 6-positions with groups selected from fluoro, chloro, bromo, lower alkyl, cyano, acylamino and trifluoromethyl, and the benzoxazole ring preferably substituted in the 5- or 6-positions with lower alkyl, lower alkoxy, phenyl, fluoro, chloro, and bromo;

$Z^3$ represents the atoms necessary to form benzothiazole, benzoselenazole, napthothiazole, naphthoselenazole, or 2-quinoline;

$Z^4$ represents the atoms necessary to form 2-quinoline;

G represents lower alkyl and, if at least one of $Z^1$ and $Z^2$ forms benzimidazole, hydrogen;

each of $R^1$, $R^2$, $R^3$ and $R^4$ represents lower alkyl or hydroxy(lower)alkyl, at least one of $R^1$ and $R^2$ and of $R^3$ and $R^4$ being preferably acid-substituted(lower)alkyl such as carboxyethyl, sulfopropyl, sulfatoethyl, etc;

X represents an acid anion; and n is 1 or 2.

Particularly effective are certain supersensitizing combinations of the above dyes, such as those described in U.S. Pat. Nos. 3,397,060; 2,688,545; 2,701,198 and 2,973,264, and their acid-substituted analogues well known in the art.

Effective blue sensitizers are simple cyanines and merocyanines of Formulas (VII) and (VIII):

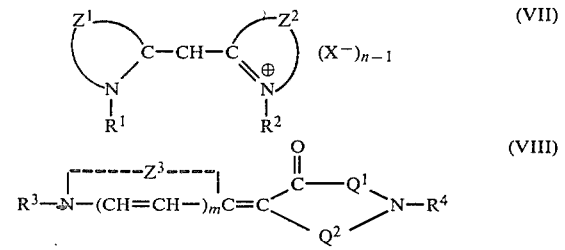

wherein:
each of $Z^1$ and $Z^2$ represents the atoms necessary to form benzothiazole, benzoselenazole, naphthothiazole and naphthoselenazole nuclei which may be substituted with groups such as chloro, methyl or methoxy, chloro, bromo, lower alkyl or lower alkoxy;

$Z^3$ represents benzothiazole, benzoselenazole which may be substituted as in $Z^1$ and $Z^2$, and pyridine nuclei;

$Q^1$ and $Q^2$ together represent the atoms necessary to complete a rhodanine, 2-thio-2,4-oxazolidine-dione or 2-thiohydantoin ring, the latter having a second nitrogen atom with a substituent $R^5$;

m represents 0 or 1;

each of $R^1$, $R^2$ and $R^3$ represents lower alkyl or hydroxy(lower)alkyl, at least one of $R^1$ and $R^2$ being preferably acid-substituted(lower)alkyl such as carboxyethyl, sulfopropyl and sulfatoethyl, etc;

$R^4$ and $R^5$ represent lower alkyl and hydroxy(lower)alkyl, and $R^4$ additionally can represent carboxyalkyl and sulfoalkyl;

X is an acid anion; and n is 1 or 2.

The photographic elements are preferably color photographic elements which form dye images through the selective destruction, formation or physical removal of dyes.

The photographic elements can produce dye images through the selective destruction of dyes or dye precursors, such as silver-dye-bleach processes, as illustrated by A. Meyer, *The Journal of Photographic Science*, Volume 13, 1965, pages 90 through 97. Bleachable azo, azoxy, xanthene, azine, phenylmethane, nitroso complex, indigo, quinone, nitro-substituted, phthalocyanine and formazan dyes, as illustrated by Stauner et al, U.S. Pat. No. 3,754,923; Piller et al, U.S. Pat. No. 3,749,576; Yoshida et al, U.S. Pat. No. 3,738,839; Froelich et al, U.S. Pat. No. 3,716,368; Piller, U.S. Pat. No. 3,655,388; Williams et al, U.S. Pat. No. 3,642,482; Gilman, U.S. Pat. No. 3,567,448; Loeffel, U.S. Pat. No. 3,443,953; Anderau, U.S. Pat. Nos. 3,443,952 and 3,211,556; Mory et al, U.S. Pat. Nos. 3,202,511 and 3,178,291; and Anderau et al, U.S. Pat. Nos. 3,178,285 and 3,178,290, as well as their hydrazo, diazonium and tetrazolium precursors and leuco and shifted derivatives, as illustrated by U.K. Pat. Nos. 923,265; 999,996 and 1,042,300; Pelz et al, U.S. Pat. No. 3,684,513; Watanabe et al, U.S. Pat. No. 3,615,493; Wilson et al, U.S. Pat. No. 3,503,741; Boes et al, U.S. Pat. No. 3,340,059; Gompf et al, U.S. Pat. No. 3,493,372; and Puschel et al, U.S. Pat. No. 3,561,970, can be employed.

The photographic elements can produce dye images through the selective formation of dyes, such as by reacting (coupling) a color-developing agent (e.g., a primary aromatic amine) in its oxidized form with a dye-forming coupler. The dye-forming couplers can be incorporated in the photographic elements, as illustrated by Schneider et al, *Die Chemie*, Volume 57, 1944, page 113; Mannes et al, U.S. Pat. No. 2,304,940; Martinez, U.S. Pat. No. 2,269,158; Jelley et al, U.S. Pat. No. 2,322,027; Frolich et al, U.S. Pat. No. 2,376,679; Fierke et al, U.S. Pat. No. 2,801,171; Smith, U.S. Pat. No. 3,748,141; Tong, U.S. Pat. No. 2,772,163; Thirtle et al, U.S. Pat. No. 2,835,579; Sawdey et al, U.S. Pat. No. 2,533,514; Peterson, U.S. Pat. No. 2,353,754; Seidel, U.S. Pat. No. 3,409,435; and Chen, *Research Disclosure*, Volume 159, July 1977, Item 15930.

In one form, the dye-forming couplers are chosen to form subtractive primary (i.e., yellow, magenta and cyan) image dyes and are nondiffusible, colorless couplers, such as two- and four-equivalent couplers of the open chain ketomethylene, pyrazolone, pyrazolotriazole, pyrazolobenzimidazole, phenol and naphthol type hydrophobically ballasted for incorporation in high-boiling organic (coupler) solvents. Such couplers are illustrated by Salminen et al, U.S. Pat. Nos. 2,423,730; 2,772,162; 2,895,826; 2,710,803; 2,407,207; 3,737,316; and 2,367,531; Loria et al, U.S. Pat. Nos. 2,772,161; 2,600,788; 3,006,759; 3,214,437; and 3,253,924; McCrossen et al, U.S. Pat. No. 2,875,057; Bush et al, U.S. Pat. No. 2,908,573; Gledhill et al, U.S. Pat. No. 3,034,892; Weissberger et al, U.S. Pat. Nos. 2,474,293; 2,407,210; 3,062,653; 3,265,506; and 3,384,657; Porter et al, U.S. Pat. No. 2,343,703; Greenhalgh et al, U.S. Pat. No. 3,127,269; Feniak et al, U.S. Pat. Nos. 2,865,748; 2,933,391; and 2,865,751; Bailey et al, U.S. Pat. No. 3,725,067; Beavers et al, U.S. Pat. No. 3,758,308; Lau, U.S. Pat. No. 3,779,763; Fernandez, U.S. Pat. No. 3,785,829; U.K. Pat. No. 969,921; U.K. Pat. No. 1,241,069; U.K. Pat. No. 1,011,940; Vanden Eynde et al, U.S. Pat. No. 3,762,921; Beavers, U.S. Pat. No. 2,983,608; Loria, U.S. Pat. Nos. 3,311,476; 3,408,194; 3,458,315; 3,447,928; and 3,476,563; Cressman et al, U.S. Pat. No. 3,419,390; Young, U.S. Pat. No. 3,419,391; Lestina, U.S. Pat. No. 3,519,429; U.K. Pat. No. 975,928; U.K. Pat. No. 1,111,554; Jaeken, U.S. Pat.

No. 3,222,176 and Canadian Pat. No. 726,651; Schulte et al, U.K. Pat. No. 1,248,924; and Whitmore et al, U.S. Pat. No. 3,227,550.

The photographic elements can incorporate alkali-soluble ballasted couplers, as illustrated by Froelich et al and Tong, cited above. The photographic elements can be adapted to form nondiffusible image dyes using dye-forming couplers in developers, as illustrated by U.K. Pat. No. 478,984; Yager et al, U.S. Pat. No. 3,113,864; Vittum et al, U.S. Pat. Nos. 3,002,836; 2,271,238; and 2,362,598; Schwan et al, U.S. Pat. No. 2,950,970; Carroll et al, U.S. Pat. No. 2,592,243; Porter et al, U.S. Pat. Nos. 2,343,703; 2,376,380; and 2,369,489; Spath, U.K. Pat. No. 886,723 and U.S. Pat. No. 2,899,306; Tuite, U.S. Pat. No. 3,152,896; and Mannes et al, U.S. Pat. Nos. 2,115,394; 2,252,718; and 2,108,602.

The dye-forming couplers upon coupling can release photographically useful fragments, such as development inhibitors or accelerators, bleach accelerators, developing agents, silver halide solvents, toners, hardeners, fogging agents, antifoggants, competing couplers, chemical or spectral sensitizers and desensitizers. Development inhibitor-releasing (DIR) couplers are illustrated by Whitmore et al, U.S. Pat. No. 3,148,062; Barr et al, U.S. Pat. No. 3,227,554; Barr, U.S. Pat. No. 3,733,201; Sawdey, U.S. Pat. No. 3,617,291; Groet et al, U.S. Pat. No. 3,703,375; Abbott et al, U.S. Pat. No. 3,615,506; Weissberger et al, U.S. Pat. No. 3,265,506; Seymour, U.S. Pat. No. 3,620,745; Marx et al, U.S. Pat. No. 3,632,345; Mader et al, U.S. Pat. No. 3,869,291; U.K. Pat No. 1,201,110; Oishi et al, U.S. Pat. No. 3,642,485; Verbrugghe, U.K. Pat. No. 1,236,767; Fujiwhara et al, U.S. Pat. No. 3,770,436; and Matsuo et al, U.S. Pat. No. 3,808,945. DIR compounds which do not form dye upon reaction with oxidized color-developing agents can be employed, as illustrated by Fujiwhara et al, German OLS No. 2,529,350 and U.S. Pat. Nos. 3,928,041; 3,958,993; and 3,961,959; Odenwalder et al, German OLS No. 2,448,063; Tanaka et al, German OLS No. 2,610,546; Kikuchi et al, U.S. Pat. No. 4,049,455; and Credner et al, U.S. Pat. No. 4,052,213. DIR compounds which oxidatively cleave can be employed, as illustrated by Porter et al, U.S. Pat. No. 3,379,529; Green et al, U.S. Pat. No. 3,043,690; Barr, U.S. Pat. No. 3,364,022; Duennebier et al, U.S. Pat. No. 3,297,445; and Rees et al, U.S. Pat. No. 3,287,129.

The photographic elements can incorporate colored dye-forming couplers, such as those employed to form integral masks for negative color images, as illustrated by Hanson, U.S. Pat. No. 2,449,966; Glass et al, U.S. Pat. No. 2,521,908; Gledhill et al, U.S. Pat. No. 3,034,892; Loria, U.S. Pat. No. 3,476,563; Lestina, U.S. Pat. No. 3,519,429; Friedman, U.S. Pat. No. 2,543,691; Puschel et al, U.S. Pat. No. 3,028,238; Menzel et al, U.S. Pat. No. 3,061,432; and Greenhalgh, U.K. Pat. No. 1,035,959; and/or competing couplers, as illustrated by Murin et al, U.S. Pat. No. 3,876,428; Sakamoto et al, U.S. Pat. No. 3,580,722; Puschel, U.S. Pat. No. 2,998,314; Whitmore, U.S. Pat. No. 2,808,329; Salminen, U.S. Pat. No. 2,742,832; and Weller et al, U.S. Pat. No. 2,689,793.

The photographic elements can produce dye images through the selective removal of dyes. Negative or positive dye images can be produced by the immobilization or mobilization of incorporated color-providing substances as a function of exposure and development, as illustrated by U.K. Pat. Nos. 1,456,413; 1,479,739; 1,475,265; and 1,471,752; Friedman, U.S. Pat. No. 2,543,691; Whitmore, U.S. Pat. No. 3,227,552; Bloom et al, U.S. Pat. No. 3,443,940; Morse, U.S. Pat. No. 3,549,364; Cook, U.S. Pat. No. 3,620,730; Danhauser, U.S. Pat. No. 3,730,718; Staples, U.S. Pat. No. 3,923,510; Oishi et al, U.S. Pat. No. 4,052,214; and Fleckenstein et al, U.S. Pat. No. 4,076,529.

The photographic elements can contain antistain agents (i.e., oxidized developing agent scavengers) to prevent developing agents oxidized in one dye image layer unit from migrating to an adjacent dye image layer unit. Such antistain agents include ballasted or otherwise nondiffusing antioxidants, as illustrated by Weissberger et al, U.S. Pat. No. 2,336,327; Loria et al, U.S. Pat. No. 2,728,659; Vittum et al, U.S. Pat. No. 2,360,290; Jelley et al, U.S. Pat. No. 2,403,721; and Thirtle et al, U.S. Pat. No. 2,701,197. To avoid autooxidation the antistain agents can be employed in combination with other antioxidants, as illustrated by Knechel et al, U.S. Pat. No. 3,700,453.

The photographic elements can include image dye stabilizers. Such image dye stabilizers are illustrated by U.K. Pat. No. 1,326,889; Lestina et al, U.S. Pat. Nos. 3,432,300 and 3,698,909; Stern et al, U.S. Pat. No. 3,574,627; Brannock et al, U.S. Pat. No. 3,573,050; Arai et al, U.S. Pat. No. 3,764,337; and Smith et al, U.S. Pat. No. 4,042,394.

This invention is particularly useful with photographic elements used in image transfer processes or in image transfer film units.

Image transfer systems include colloid transfer systems, as illustrated by Yutzy et al, U.S. Pat. Nos. 2,596,756 and 2,716,059; imbibition transfer systems, as illustrated by Minsk, U.S. Pat. No. 2,882,156; and color image transfer systems, as illustrated by *Research Disclosure*, Volume 151, November 1976, Item 15162, and Volume 123, July 1974, Item 12331.

Color image transfer systems (including emulsion layers, receiving layers, timing layers, acid layers, processing compositions, supports and cover sheets) and the images they produce can be varied by choosing among a variety of features, combinations of which can be used together as desired.

Film units can be chosen which are either integrally laminated or separated during exposure, processing and/or viewing, as illustrated by Rogers, U.S. Pat. No. 2,983,606; Beavers et al, U.S. Pat. No. 3,445,228; Whitmore, Canadian Pat. No. 674,082; Friedman et al, U.S. Pat. No. 3,309,201; Land, U.S. Pat. Nos. 2,543,181; 3,053,659; 3,415,644; 3,415,645; and 3,415,646; and Barr et al, U.K. Pat. No. 1,330,524.

A variety of approaches are known in the art for obtaining transferred dye images. Transferred dye images are obtained by altering the initial mobility of dye image providing compounds. (Initial mobility refers to the mobility of the dye image providing compound when it is contacted by the processing solution. Initially mobile dye image providing compounds as coated do not migrate prior to contact with processing solution.)

Dye image providing compounds are classified as either positive-working or negative-working. Positive-working dye image providing compounds are those which produce a positive transferred dye image when employed in combination with a conventional, negative-working silver halide emulsion. Negative-working dye image providing compounds are those which produce a negative transferred dye image when employed in combination with conventional, negative-working silver halide emulsions. (The foregoing definitions assume the absence of special image reversing techniques, such as those referred to in *Research Disclosure*, Vol. 176, December 1978, Item 17643, paragraph XXIII-E.) When, as in the present invention, the silver halide emulsions are direct-positive emulsions, positive-working dye image providing compounds produce negative transferred dye images and negative-working dye image providing compounds produce positive transferred dye images.

Image transfer systems, which include both the dye image providing compounds and the silver halide emulsions, are positive-working when the transferred dye image is positive and negative-working when the transferred dye image is negative. When a retained dye image is formed, it is opposite in sense to the transferred dye image.

A variety of dye image providing compounds are known and can be employed in the practice of this invention. One approach is to employ ballasted dye-forming (chromogenic) or non-dye-forming (non-chromogenic) couplers having a mobile dye attached at a coupling-off site. Upon coupling with an oxidized color developing agent, such as a para-phenylenediamine, the mobile dye is displaced so that it can transfer to a receiver. Such negative-working dye image providing compounds are illustrated by Whitmore et al, U.S. Pat. No. 3,227,550; Whitmore, U.S. Pat. No. 3,227,552; and Fujiwhara et al, U.K. Pat. No. 1,445,797, the disclosures of which are here incorporated by reference.

In a preferred image transfer system according to this invention employing negative-working dye image providing compounds, a cross-oxidizing developing agent (electron transfer agent) develops silver halide and then cross-oxidizes with a compound containing a dye linked through an oxidizable sulfonamido group, such as a sulfonamidophenol, sulfonamidoaniline, sulfonamidoanilide, sulfonamidopyrazolobenzimidazole, sulfonamidoindole or sulfonamidopyrazole. Following cross-oxidation, hydrolytic deamidation cleaves the mobile dye with the sulfonamido group attached. Such systems are illustrated by Fleckenstein, U.S. Pat. Nos. 3,928,312 and 4,053,312; Fleckenstein et al, U.S. Pat. No. 4,076,529; Melzer et al, U.K. Pat. No. 1,489,694; Degauchi, German OLS No. 2,729,820; Koyama et al, German OLS No. 2,613,005; Vetter et al, German OLS No. 2,505,248; and Kestner et al, *Research Disclosure*, Volume 151, November 1976, Item 15157. Also specifically contemplated are otherwise similar systems which employ an immobile, dye-releasing (a) hydroquinone, as illustrated by Gompf et al, U.S. Pat. No. 3,698,897 and Anderson et al, U.S. Pat. No. 3,725,062; (b) para-phenylenediamine, as illustrated by Whitmore et al, Canadian Pat. No. 602,607; or (c) quaternary ammonim compound, as illustrated by Becker et al, U.S. Pat. No. 3,728,113.

Another specifically contemplated dye image transfer system which employs negative-working dye image providing compounds reacts an oxidized electron transfer agent or, specifically, in certain forms, an oxidized para-phenylenediamine with a ballasted phenolic coupler having a dye attached through a sulfonamido linkage. Ring closure to form a phenazine releases mobile dye. Such an imaging approach is illustrated by Bloom et al, U.S. Pat. Nos. 3,443,939 and 3,443,940.

In still another image transfer system employing negative-working dye image providing compounds, ballasted sulfonylamidrazones, sulfonylhydrazones or sulfonylcarbonylhydrazides can be reacted with oxidized para-phenylenediamine to release a mobile dye to be transferred, as illustrated by Puschel et al, U.S. Pat. Nos. 3,628,952 and 3,844,785. In an additional image transfer system, a hydrazide can be reacted with silver halide having a developable latent image site and thereafter decompose to release a mobile, transferable dye, as illustrated by Rogers, U.S. Pat. No. 3,245,789; Kohara et al, *Bulletin Chemical Society of Japan*, Volume 43, pages 2433 through 2437; and Lestina et al, *Research Disclosure*, Volume 28, December 1974, Item 12832.

The foregoing systems all employ initially immobile negative-working dye image providing compounds containing a preformed dye which is split off during imaging. The released dye is mobile and can be transferred to a receiver. Positive-working dye image providing systems which split off mobile dyes from immobile initially present compounds are also known. For example, it is known that when silver halide is imagewise developed, the residual silver ions associated with the undeveloped silver halide can react with a dye substituted ballasted thiazolidine to release a mobile dye imagewise, as illustrated by Cieciuch et al, U.S. Pat. No. 3,719,489 and Rogers, U.S. Pat. No. 3,443,941.

Preferred initially immobile positive-working dye image providing compounds are those which release mobile dye by anchimeric displacement reactions. The compound in its initial form is hydrolyzed to its active form while silver halide development with an electron transfer agent is occurring. Cross-oxidation of the active dye-releasing compound by the oxidized electron transfer agent prevents hydrolytic cleaving of the dye moiety. Benzisoxazolone precursors of hydroxylamine dye-releasing compounds are illustrated by Hinshaw et al, U.K. Pat. No. 1,464,104 and *Research Disclosure*, Volume 144, April 1976, Item 14447. N-Hydroquinonyl carbamate dye image providing compounds are illustrated by Fields et al, U.S. Pat. No. 3,980,479. Image transfer systems are also known in which an immobile reducing agent (electron donor) is employed in combination with an immobile ballasted electron-accepting nucleophilic displacement (BEND) compound which, on reduction, anchimerically displaces a diffusible dye. Hydrolysis of the electron donor precursor to its active form occurs simultaneously with silver halide development by an electron transfer agent. Cross-oxidation of the electron donor with the oxidized electron transfer agent prevents further reaction. Cross-oxidation of the BEND compound with the residual, unoxidized electron donor then occurs. Anchimeric displacement of mobile dye from the reduced BEND compound occurs as part of a ring closure reaction. A system of this type is illustrated by Chasman et al, U.S. Pat. No. 4,139,379, issued Feb. 13, 1979.

Other positive-working, initially immobile, dye image providing compounds are illustrated by Rogers, U.S. Pat. No. 3,185,567 and U.K. Pat. Nos. 880,233 and '234.

A variety of image transfer systems are known in which a positive-working dye image providing compound containing a dye or dye precursor is initially mobile, but can be imagewise immobilized by reduction of developable silver halide directly or indirectly through an electron transfer agent. Systems which employ mobile dye developers, including shifted dye developers, are illustrated by Rogers, U.S. Pat. Nos. 2,774,668 and 2,983,606; Idelson et al, U.S. Pat. No. 3,307,947; Dershowitz et al, U.S. Pat. No. 3,230,085; Cieciuch et al, U.S. Pat. No. 3,579,334; Yutzy, U.S. Pat.

No. 2,756,142; and Harbison, Defensive Publication No. T889,017. In a variant form a dye moiety can be attached to an initially mobile coupler. Oxidation of a para-phenylenediamine or hydroquinone developing agent can result in a reaction between the oxidized developing agent and the dye containing a coupler to form an immobile compound. Such systems are illustrated by Rogers, U.S. Pat. Nos. 2,774,668 and 3,087,817; Greenhalgh et al, U.K. Pat. Nos. 1,157,501 and '506; Puschel et al, U.S. Pat. No. 3,844,785; Stewart et al, U.S. Pat. No. 3,653,896; Gehin et al, French Pat. No. 2,287,711; and *Research Disclosure, Volume* 145, May 1976, Item 14521.

Other image transfer systems are known in which varied immobilization or transfer techniques are employed. For example, a mobile developer-mordant can be imagewise immobilized by development of silver halide to imagewise immobilize an initially mobile dye, as illustrated by Haas, U.S. Pat. No. 3,729,314. Silver halide development with an electron transfer agent can produce a free radical intermediate which causes an initially mobile dye to polymerize in an imagewise manner, as illustrated by Pelz et al, U.S. Pat. No. 3,585,030 and Oster, U.S. Pat. No. 3,019,104. Tanning development of a gelatino-silver halide emulsion can render the gelatin impermeable to mobile dye and thereby imagewise restrain transfer of mobile dye, as illustrated by Land, U.S. Pat. No. 2,543,181. Also gas bubbles generated by silver halide development can be used effectively to restrain mobile dye transfer, as illustrated by Rogers, U.S. Pat. No. 2,774,668. Electron transfer agent not exhausted by silver halide development can be transferred to a receiver to imagewise bleach a polymeric dye to a leuco form, as illustrated by Rogers, U.S. Pat. No. 3,015,561.

A number of image transfer systems employing positive-working dye image providing compounds are known in which dyes are not initially present, but are formed by reactions occurring in the photographic element or receiver following exposure. For example, a mobile coupler and color developing agent can be imagewise reacted as a function of silver halide development to produce an immobile dye while residual developing agent and coupler are transferred to the receiver, and the developing agent is oxidized to form on coupling a transferred immobile dye image, as illustrated by Yutzy, U.S. Pat. No. 2,756,142; Greenhalgh et al, U.K. Pat. Nos. 1,157,501-506 and Land, U.S. Pat. Nos. 2,559,643; 2,647,049; 2,661,293; 2,698,244; and 2,698,798. In a variant form of this system, the coupler can be reacted with a solubilized diazonium salt (or azosulfone precursor) to form a diffusible azo dye before transfer, as illustrated by Viro et al, U.S. Pat. No. 3,837,852. In another variant form, a single, initially mobile coupler-developer compound can participate in intermolecular self-coupling at the receiver to form an immobile dye image, as illustrated by Simon, U.S. Pat. No. 3,537,850 and Yoshiniobu, U.S. Pat. No. 3,865,593. In still another variant form, a mobile amidrazone is present with the mobile coupler and reacts with it at the receiver to form an immobile dye image, as illustrated by Janssens et al, U.S. Pat. No. 3,939,035. Instead of using a mobile coupler, a mobile leuco dye can be employed. The leuco dye reacts with oxidized electron transfer agent to form an immobile product, while unreacted leuco dye is transferred to the receiver and oxidized to form a dye image, as illustrated by Lestina et al, U.S. Pat. No. 3,880,658; Cohler et al, U.S. Pat. No. 2,892,710; Corley et al, U.S. Pat. No. 2,992,105; and Rogers, U.S. Pat. Nos. 2,909,430 and 3,065,074. Mobile quinone-heterocyclammonium salts can be immobilized as a function of silver halide development and residually transferred to a receiver where conversion to a cyanine or merocyanine dye occurs, as illustrated by Bloom, U.S. Pat. Nos. 3,537,851 and '852.

Image transfer systems employing negative-working dye image providing compounds are also known in which dyes are not initially present, but are formed by reactions occurring in the photographic element or receiver following exposure. For example, a ballasted coupler can react with color developing agent to form a mobile dye, as illustrated by Whitmore et al U.S. Pat. No. 3,227,550, Whitmore U.S. Pat. No. 3,227,552, Bush et al U.S. Pat. No. 3,791,827 and Viro et al U.S. Pat. No. 4,036,643. An immobile compound containing a coupler can react with oxidized para-phenylenediamine to release a mobile coupler which can react with additional oxidized para-phenylenediamine before, during or after release to form a mobile dye, as illustrated by Figueras et al U.S. Pat. No. 3,734,726 and Janssens et al German OLS No. 317,134. In another form, a ballasted amidrazone reacts with an electron transfer agent as a function of silver halide development to release a mobile amidrazone which reacts with a coupler to form a dye at the receiver, as illustrated by Ohyama et al U.S. Pat. No. 3,933,493.

An image to be viewed can be transferred from the image-forming layers. A retained image can be formed for viewing as a concurrently formed complement of the transferred image. Positive transferred images and useful negative retained images can be formed with the direct positive silver halide emulsions of this invention when imaging chemistry is negative-working; and negative transferred images and positive retained images can be formed when the imaging chemistry is positive-working. Images retained in and transferred from the image-forming layers are illustrated by U.K. Pat. No. 1,456,413, Friedman U.S. Pat. No. 2,543,691, Bloom et al U.S. Pat. No. 3,443,940, Staples U.S. Pat. No. 3,923,510 and Fleckenstein et al U.S. Pat. No. 4,076,529.

Where mobile dyes are transferred to the receiver a mordant is commonly present in a dye image providing layer. Mordants and mordant containing layers are described in the following references which are incorporated by reference: Sprague et al U.S. Pat. No. 2,548,564, Weyerts U.S. Pat. No. 2,548,575, Carroll et al U.S. Pat. No. 2,675,316, Yutzy et al U.S. Pat. No. 2,713,305, Saunders et al U.S. Pat. No. 2,756,149, Reynolds et al U.S. Pat. No. 2,768,078, Gray et al U.S. Pat. No. 2,839,401, Minsk U.S. Pat. Nos. 2,882,156 and 2,945,006, Whitmore et al U.S. Pat. No. 2,940,849, Condax U.S. Pat. No. 2,952,566, Mader et al U.S. Pat. No. 3,016,306, Minsk et al U.S. Pat. Nos. 3,048,487 and 3,184,309, Bush U.S. Pat. No. 3,271,147, Whitmore U.S. Pat. No. 3,271,148, Jones et al U.S. Pat. No. 3,282,699, Wolf et al U.S. Pat. No. 3,408,193, Cohen et al U.S. Pat. Nos. 3,488,706, 3,557,066, 3,625,694, 3,709,690, 3,758,445, 3,788,855, 3,898,088 and 3,944,424, Cohen U.S. Pat. No. 3,639,357, Taylor U.S. Pat. No. 3,770,439, Campbell et al U.S. Pat. No. 3,958,995 and Ponticello et al *Research Disclosure,* Vol. 120, April 1974, Item 12045, as well as Campbell et al U.S. Ser. No. 906,289, filed May 15, 1978, the disclosure of which is also here incorporated by reference.

One-step processing can be employed, as illustrated by U.K. Pat. No. 1,471,752, Land U.S. Pat. No.

2,543,181, Rogers U.S. Pat. No. 2,983,606 (pod processing), Land U.S. Pat. No. 3,485,628 (soak image-former and laminate to receiver) and Land U.S. Pat. No. 3,907,563 (soak receiver and laminate to image-forming element) or multi-step processing can be employed, as illustrated by Yutzy U.S. Pat. No. 2,756,142, Whitmore et al U.S. Pat. No. 3,227,550 and Faul et al U.S. Pat. No. 3,998,637.

Preformed reflective layers can be employed, as illustrated by Whitmore Canadian Pat. No. 674,082, Beavers U.S. Pat. No. 3,445,228 Land U.S. Pat. Nos. 2,543,181, 3,415,644, '645 and '646 and Barr et al U.K. Pat. No. 1,330,524 or processing-formed reflective layers can be employed, as illustrated by Land U.S. Pat. Nos. 2,607,685 and 3,647,437, Rogers U.S. Pat. No. 2,983,606 and Buckler U.S. Pat. No. 3,661,585.

Generally, the image transfer film units in accordance with this invention comprise:

(1) a photographic element comprising a support having thereon at least one silver halide emulsion layer containing radiation-sensitive internal latent image silver halide grains and a thiazole-substituted aryl-hydrazide nucleating agent, the emulsion layer preferably having in contact therewith an image dye-providing material, (2) an image-receiving layer, which can be located on a separate support and superposed or adapted to be superposed on the photographic element or, preferably, can be coated as a layer in the photographic element, (3) an alkaline processing composition, (4) means containing and adapted to release the alkaline processing composition into contact with the emulsion layer, and (5) a silver halide developing agent located in at least one of the photographic element and alkaline processing composition so that the processing composition and developing agent, when brought together, form a silver halide surface developer.

In highly preferred embodiments, the film units of this invention contain a support having thereon a layer containing a blue-sensitive emulsion and in contact therewith a yellow image dye-providing material, a red-sensitive silver halide emulsion and in contact therewith a cyan image dye-providing material, and a green-sensitive emulsion and in contact therewith a magenta image dye-providing material, and preferably all of said image dye-providing materials are initially immobile image dye-providing materials.

The terms "diffusible" (or "mobile") and "immobile" (or "nondiffusible"), as used herein, refer to compounds which are incorporated in the photographic element and, upon contact with an alkaline processing solution, are substantially diffusible or substantially immobile, respectively, in the hydrophilic colloid layers of a photographic element.

The term "image dye-providing material", as used herein, is understood to refer to those compounds which are employed to form dye images in photographic elements. These compounds include dye developers, shifted dyes, color couplers, oxichromic compounds, dye redox releasers, etc, as described above in connection with positive-working and negative-working image transfer systems.

In one preferred embodiment, the receiver layer is coated on the same support with the photosensitive silver halide emulsion layers, the support is preferably a transparent support, an opaque layer is preferably positioned between the image-receiving layer and the photosensitive silver halide layer, and the alkaline processing composition preferably contains an opacifying substance, such as carbon or a pH-indicator dye which is discharged into the film unit between a dimensionally stable support to cover sheet and the photosensitive element.

In certain embodiments, the cover sheet can be superposed or is adapted to be superposed on the photosensitive element. The image-receiving layer can be located on the cover sheet so that it becomes an image-receiving element. In certain preferred embodiments where the image-receiving layer is located in the photosensitive element, a neutralizing layer is located on the cover sheet.

Increases in $D_{max}$ can be obtained in color image transfer film units containing internally sulfur- and gold-sensitized emulsions of the type described by Evans, U.S. Pat. No. 3,761,276, and sulfonamidonaphthol redox dye-releasing compounds of the type described by Fleckenstein British Pat. No. 1,405,662, by incorporation into the emulsion layers of a variety of chemical addenda generally recognized in the art as antifoggants or development inhibitors, as well as hydrolyzable precursors thereof. Many of these compounds also provide improved stabilization of sensitometric properties of liquid emulsion and of the storage life of the coated emulsion. The effects, shown in film units of the type described in Examples 40 through 42 of British Pat. No. 1,405,662, are in addition to the effect of 5-methylbenzotriazole in the processing composition even when the latter is present in quantities as high as 4 grams per liter. Effective compounds in general are selected from the group consisting of (a) 1,2,3-triazoles, tetrazoles and benzotriazoles having an $N-R^1$ group in the heterocyclic ring, wherein $R^1$ represents hydrogen or an alkali-hydrolyzable group, or (b) heterocyclic mercaptans or thiones and precursors thereof, mostly having one of the formulas

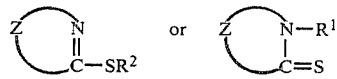

wherein
Z comprises the atoms necessary to complete an azole ring, and
$R^2$ represents, in addition to the groups specified above for $R^1$, a metal ion.

The compounds are generally employed at concentrations less than about 300 mg per mole of silver, each compound having an optimum concentration above which development and/or nucleation are inhibited and $D_{max}$ decreases with increasing concentration. Specifically preferred antifoggants and stabilizers, as well as other preferred color image transfer film unit and system features, are more specifically disclosed in *Research Disclosure*, Volume 151, November 1976, Item 15162, the disclosure of which is hereby incorporated by reference.

A more detailed description of useful image transfer film units and systems is contained in the patents relating to image transfer cited above, the disclosures of which are here incorporated by reference. A specific, preferred image-transfer film unit and image transfer system is that disclosed by Leone et al U.S. Pat. Nos. 4,030,925 and 4,080,207, cited above, and here incorporated by reference.

The following examples illustrate the invention. All temperatures are in °C.

EXAMPLE 1

N-(Benzotriazol-5-yl)-4-(2-formylhydrazino)-phenylacetamide

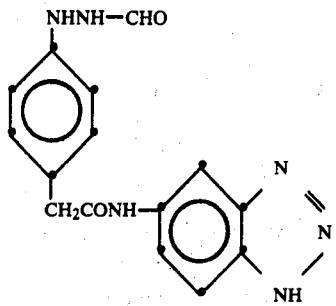

p-(2-Formylhydrazino)phenylacetic Acid p-Aminophenylacetic acid (3.02 g, 0.02 M) and concentrated hydrochloric acid (8 ml) were stirred together at 0°. The mixture was treated with sodium nitrite (1.38 g, 0.02 M) in water (10 ml) at 0°. The reaction mixture was then stirred for a further one-half hour.

Stannous chloride (13.3 g, 0.07 M) in concentrated hydrochloric acid (15 ml) was added dropwise to the diazotized solution at 0°. The reaction mixture was refrigerated overnight. Next morning, the solid was filtered, washed with a saturated solution of sodium chloride (30 ml), followed by petroleum-ether and ether. The solid was taken up in ice-cold water (20 ml) and sodium hydroxide (3 N) solution was added until all of the solid was in solution. This was then acidified with acetic acid and was filtered immediately. The filtrate was concentrated to precipitate the hydrazine. The hydrazine was filtered and dried (2.63 g, 80 percent).

p-Hydrazinophenylacetic acid (3.32 g, 0.02 M), sodium formate (2.72 g, 0.04 m), ethyl formate (49 g), formic acid (10 ml) was refluxed for one hour in ethanol (100 ml). The residue was removed by filtration and the filtrate on concentration afforded light-yellow crystals (2.2 g, 55 percent).

5-Aminobenzotriazole

5-Nitrobenztriazole (10 g) was shaken with Raney nickel (3 spoons) and ethanol (200 ml) under hydrogen at atmospheric pressure until the uptake of hydrogen ceased. The Raney nickel was removed by filtration through Keiselguhr, and the dark ethanolic solution was evaporated to dryness. Crystallization from aqueous ethanol afforded 5-aminobenzotriazole (6 g, 75 percent).

N-(Benzotriazol-5-yl)-4-(2-formylhydrazino)-phenylacetamide

5-Aminobenzotriazole (2.68 g, 0.02 M) in dimethylformamide (20 ml) was stirred at room temperature overnight with the hydrazide (3.98 g, 0.02 M) in the presence of dicyclohexylcarbodiimide (4.12 g, 0.02 M). Next morning, dicyclohexylurea was removed by filtration and the filtrate was poured onto ice and hydrochloric acid (10 ml). The solid so formed was collected by filtration, washed with ice-cold water, and was dried (4 g, 66 percent). Recrystallization from pyridine gave (1.2 g, 20 percent). The identity of the compound was confirmed by NMR, mass spectra and elemental analysis.

EXAMPLE 2

A coating was prepared as follows:

A dispersion of an image dye-releasing compound of the structure:

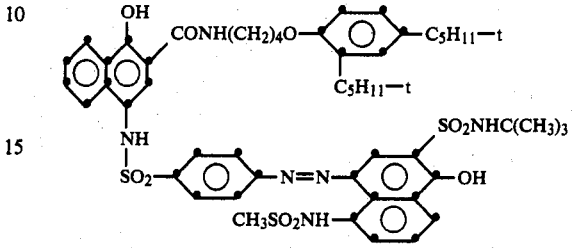

in diethyllauramide (1:1) was made in aqueous gelatin, and coated on a polyethylene terephthalate photographic film base to give coverages of 0.5 grams per square meter of dye releaser and 1.0 grams per square meter of gelatin. The dispersion particles were of the order of 1 μm average diameter.

On top of this layer was coated an emulsion layer. This was a 1.4-micron green-sensitized silver bromide emulsion of the internal image type, as described in British Pat. No. 1,385,039, coated at 1 gram per square meter of silver bromide and 1 gram per square meter of gelatin and containing 5-sec-octadecylhydroquinone-2-sulphonic acid at 2 grams per mol Ag.

The dried coating was exposed to a sensitometric light source, under safelight conditions, and processed by dipping it and a receiving sheet into a developer solution for 15 seconds, then removing the two sheets and squeegeeing them into intimate face-to-face contact for a further one minute and 45 seconds. The two sheets were then peeled apart and the magenta dye image on the receiving sheet examined. The receiving sheet consisted of poly[styrene-co-N,N-dimethyl-N-benzyl-N-(3-maleimidopropyl)ammonium chloride] in gelatin coated on polyethylene-coated paper both at 2 grams per square meter.

The developer solution used had the following composition:

| | | |
|---|---|---|
| $Na_2HPO_4$ | 36 | g/l |
| $Na_2SO_3$ | 25 | g/l |
| Phenoxyethanol | 6.6 | ml/l |
| Ethoxyethanol | 3.3 | ml/l |
| Ethanolamine | 4 | ml/l |
| 4-Hydroxymethyl-4-methyl-1-phenyl-3-pyrazolidone | 0.60 | g/l |
| Piperidinohexosereductone | 2.0 | g/l |
| Benzotriazole | 0.10 | g/l |
| Water to make | 1 | liter |
| 4M NaOH solution to | pH 12.0 | |

The nucleating agent of Example 1 and a control nucleating agent were dissolved in this solution at the levels stated below.

Direct-positive magenta images-on-white of the sensitometric step-wedge were obtained, and the diffuse reflection densities to green light read. Results are given in Table I.

TABLE I

| Nucleator | Concentration | $D_{max}$ | $D_{min}$ |
|---|---|---|---|
| 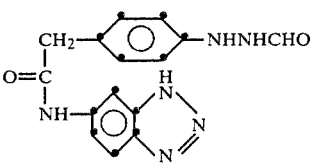 (I) | 1.5 mg/l<br>2.5 mg/l<br>5 mg/l<br>10 mg/l<br>20 mg/l | 1.22<br>1.85<br>2.04<br>2.30<br>2.35 | 0.29<br>0.31<br>0.36<br>0.42<br>0.54 |
| 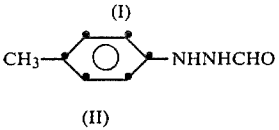 (II) | 10 mg/l<br>25 mg/l<br>50 mg/l<br>100 mg/l | 0.89<br>1.62<br>1.65<br>1.80 | 0.21<br>0.24<br>0.24<br>0.24 |

From these results, it can be seen that the nucleator of the invention (I) is clearly active at much lower concentrations than the non-adsorbing nucleator (II).

EXAMPLE 3

Coatings were prepared as in Example 2, except that immediately before coating the emulsion layer, compound (I) was added (as a solution in methanol) to the emulsion at 30 mg per mol of AgBr in one case, and at 100 mg per mol of AgBr in the other. Testing and processing were as in Example 2, except that no nucleator was added to the developer solution. Direct positive images in magenta dye were obtained in each case, with $D_{max}/D_{min}$ 1.40/0.43 and 1.60/0.39, respectively.

EXAMPLE 4

N-(Benzotriazol-5-yl)-3-[5-(2-formylhydrazino)-2-methoxyphenyl]propionamide

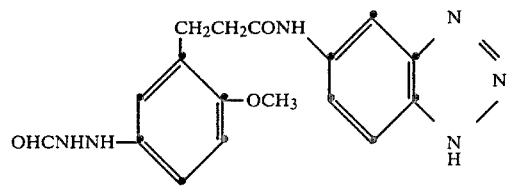

2-Methoxy-5-nitrobenzaldehyde

Finely-divided 2-methoxybenzaldehyde (49 g) was added to ice-cold concentrated sulphuric acid (95 ml) and the mixture was stirred to give a deep red solution which was cooled to −5°. The mixture was cooled in a CO₂/acetone bath while fuming nitric acid (sp.gr. 1.5; 20 ml) was added dropwise with stirring whilst the temperature of the reaction remained below 10°.

On completion of the addition, the mixture was stirred for a further 15 minutes and then poured into ice/water (2 liters). A fawn powder was obtained by filtration and this was recrystallized from boiling ligroin (5 liters).

Weight of product = 28 grams.

2-Methoxy-5-nitrocinnamic acid

Piperidine (1 ml) was added to a mixture of 2-methoxy-5-nitrobenzaldehyde (24 g) and malonic acid (30 g) in pyridine (about 60 ml). The mixture was warmed on a steam bath for 3 hours (slow evolution of carbon dioxide) and then poured into water (500 ml) when a yellow solid precipitated. The solid was removed by filtration and crystallized from ethanol (1 liter). The weight of the product was 20 grams.

3-(5-Amino-2-methoxyphenyl)propionic acid

2-Methoxy-5-nitrocinnamic acid (17 g) and 10 percent Palladium on charcoal catalyst (2 g) in ethanol (600 ml) were hydrogenated under a pressure of 50 psi of hydrogen.

When the uptake of hydrogen was complete, the ethanolic solution was treated with decolorizing charcoal (5 g) and then filtered through Kieselguhr. The filtrate was evaporated to dryness to give a cream powder. The weight of product was 13.7 g.

3-[5-(2-Formylhydrazino)-2-methoxyphenyl]propionic acid 3-(5-Amino-2-methoxyphenyl)propionic acid (4 g, 0.02 mole), concentrated hydrochloric acid (30 ml) and water (45 ml) were stirred together at 0°. The mixture was treated with sodium nitrite (1.38 g, 0.02 mole) in water (10 ml) at 0°. The solution was then stirred for a further one-half hour. The excess of nitrous acid was destroyed with urea. The above reaction mixture was added to a solution of stannous chloride (7.6 g) in concentrated hydrochloric acid (10 ml). The precipitate (5 g) was collected by filtration. Free hydrazine was obtained from a concentrated aqueous solution of the crude hydrochloride by addition of saturated aqueous solution of sodium acetate. A mixture of 3-(5-hydrazino-2-methoxyphenyl)propionic acid (8.8 g, 0.025 mole), sodium formate (2.8 g, 0.04 mole), formic acid (18 ml) and ethanol (60 ml) was heated under reflux for one hour. The solvents were removed under vacuum and the residue was dissolved in ethyl acetate (1 liter). The organic layer was then washed with water and dilute aqueous hydrochloric acid (1 percent). The organic layer was dried with sodium sulphate, the solvent was removed under reduced pressure and the residue crystallized from water (5 g).

N-(Benzotriazol-5-yl)-3-[5-(2-formylhydrazino)-2-methoxyphenyl]propionamide

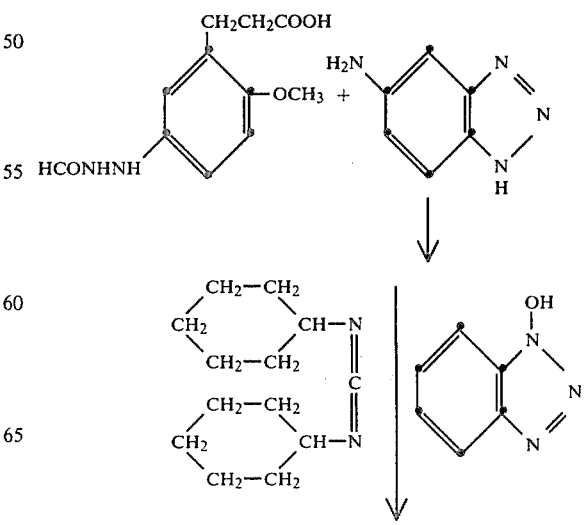

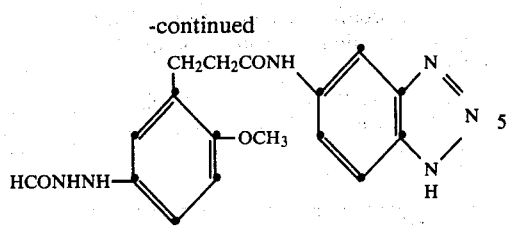

The preparation was carried out by stirring the reactants together under nitrogen with the exclusion of moisture.

Anhydrous N-hydroxybenzotriazole (1.3 g) was added to a cooled solution of 3-[5-(2-formylhydrazino)-2-methoxyphenyl]propionic acid (1.2 g) and 5-aminobenzotriazole (0.67 g, 0.005 mole) in dry dimethylformamide (10 ml). A solution of dicyclohexylcarbodi-imide (1.1 g) was added dropwise to the solution of reactants at such a rate that the temperature was kept at 0°.

After the addition, the reaction mixture was kept for one hour at 0°, 15 hours at room temperature and 6 hours at 60° C.

The main crop of urea was collected after 16 hours but a small amount precipitated after cooling of the reaction mixture. The filtrate was concentrated in vacuo and the resulting oil was dissolved in methanol. On cooling, the cream-colored product crystallized out. A sample recrystallized from methanol (0.9 g).

$C_{17}H_{18}N_6O_3$ Requires: C, 57.6; H, 5.0; H, 23.7. Found: C, 57.2; H, 5.2; N, 23.4.

EXAMPLE 5

N-(Benzotriazol-5-yl)-4-(2-acetylhydrazino)phenoxyacetamide

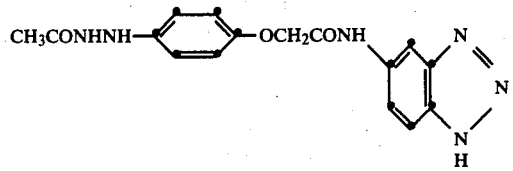

4-(2-Acetylhydrazino)phenoxyacetic acid

4-Hydrazinophenoxyacetic acid $0.1H_2O$ (10.0 g) and 1,3,4,6-tetraacetyltetrahydroimidazo[4,5-d]imidazole-2,5-(1H,3H)-dione (7.8 g) were suspended in dry acetonitrile (200 ml) containing acetic acid (1 ml). The mixture was heated under reflux for 3 hours, cooled to room temperature, and filtered. The precipitate was washed well with acetonitrile; the washings were combined with the filtrate, and this solution was evaporated to give a dark oil. The residue was taken up in hot ethanol (25 ml) and the brownn powder which precipitated on chilling was filtered off and dried. Recrystallization from acetonitrile gave the product as chunky, tan crystals (6.9 g).

N-(Benzotriazol-5-yl)-4-(2-acetylhydrazino)phenoxyacetamide

A solution of 4-(2-acetylhydrazino)phenoxyacetic acid (1.1 g), N-hydroxybenzotriazole (1.0 g) and 5-aminobenzotriazole (0.67 g, 0.005 mole) in dry dimethylformamide (10 ml) was stirred at 0° under dry nitrogen. Dicyclohexylcarbodiimide (1.1 g) in dry dimethylformamide (5 ml) was added dropwise over 15 minutes and the reaction mixture was stirred for 1 hour at 0° and 4 hours at room temperature. The dicyclohexylurea which precipitated was filtered and dried (0.7 g) and the filtrate was stirred at 60° overnight, under nitrogen. The reaction mixture was cooled and an additional precipitate of dicyclohexylurea was filtered off (0.3 g). The filtrate was evaporated, the residue was triturated with boiling methanol (50 ml) and the solid which precipitated was filtered off and dried (0.7 g). The filtrate was cooled at 5° overnight and the solid which crystallized out was filtered off and dried (0.6 g). The two precipitates, which were identical by IR, were combined and recrystallized from methanol:acetonitrile to give the product was a beige-colored powder (1.0 g). NMR analysis indicates the presence of ca 0.3 mole of $H_2O$.

$C_{16}H_{16}N_6O_3 + 0.3\ H_2O$ Requires: C, 55.58; H, 4.81; N, 24.61. Found: C, 55.57; H, 4.86; N, 24.32.

EXAMPLE 6

A dispersion of the redox dye releaser specified in Example 2 was made and coated as described therein.

On top of this layer was coated the emulsion layer described in Example 2.

The dried coating was exposed to a sensitometric light source, under safelight conditions, and processed by dipping it and a receiving sheet into a developer solution for 15 seconds, then removing the two sheets and squeegeeing them into intimate face-to-face contact for a further 1 minute and 45 seconds. The two sheets were then peeled apart and the magenta dye image on the receiving sheet examined. (The receiving sheet consisted of poly[styrene-co-N,N-dimethyl-N-benzyl-N-(3-maleimidopropyl)ammonium chloride] in gelatin coated on polyethylene-coated paper both at 2 grams per square meter, and hardened with 0.02 grams per square meter of bis(vinylsulphonylmethyl)ether hardening agent.)

The developer solution used had the following composition:

| | | |
|---|---|---|
| $Na_2HPO_4$ | 36 | g/l |
| $Na_2SO_3$ | 25 | g/l |
| Benzyl alcohol | 10 | ml/l |
| L-Lysine hydrochloride | 5 | g/l |
| 4-Hydroxymethyl-4-methyl-1-phenyl-3-pyrazolidone | 0.60 | g/l |
| Piperidinohexosereductone | 2.0 | g/l |
| 5-Methylbenzotriazole | 0.20 | g/l |
| Water to make | 1 | liter |
| 4M sodium hydroxide solution to pH | 12.0 | |

The nucleating agent prepared in Example 5 was dissolved in this solution at the levels stated below.

Direct-positive magenta images-on-white of the sensitometric step-wedge were obtained, and the diffuse reflection densities to green light read. The results are given in Table II.

TABLE II

| Nucleator Concentration | Minimum Density | Maximum Density |
|---|---|---|
| 0 | 0.32 | 0.70 |
| 2 mg/l | 0.38 | 1.28 |
| 5 mg/l | 0.57 | 1.70 |
| 10 mg/l | 0.77 | 1.78 |

Thus, a preferred level of nucleation was obtained at a concentration of 5 mg/l under the conditions of the experiment.

EXAMPLE 7

In this and the following Example, the nucleators of Examples 1 and 4 were tested in a series of photographic coatings. Each coating consisted of a support having coated thereon a first layer comprising a dispersion of the redox dye-releaser specified in Example 2, and a second layer comprising the green-sensitized internal image silver bromide emulsion employed in Example 2 containing one of the nucleating agents.

To portions of the emulsion were added quantities of nucleating agent, dissolved in methanol (with a little dimethylformamide in the case of nucleator of Example 1), as specified in Table III. The portions of emulsion were then coated separately (1 gram of silver/m²) on top of the redox dye releaser layer described above, and the emulsion layers in turn were supercoated with a layer comprising gelatin, 1 g/m².

A portion of each dried coating was exposed to a sensitometric light source, under safelight conditions, and processed by dipping it and a receiving sheet into an activator solution for 15 seconds at 22°, then removing the two sheets and squeegeeing them into intimate face-to-face contact for a further 1 minute and 45 seconds. The two sheets were then peeled apart and the magenta dye image on the receiving sheet examined. (The receiving sheet consisted of poly[styrene-co-N,N-dimethyl-N-benzyl-N-(3-maleimidopropyl)ammonium chloride] 2 g/m² gelatin, 2 g/m², 4-hydroxymethyl-4-methyl-1-phenyl-3-pyrazolidone, 0.25 g/m², and bis(vinylsulphonylmethyl)ether hardening agent, 0.02 g/m², coated on polyethylene-coated paper.)

The activator solution used had the following composition:

| | | |
|---|---|---|
| Na₂CO₃ | 28 | g |
| Lysine hydrochloride | 5 | g |
| Benzyl alcohol | 10 | ml |
| 5-Methylbenzotriazole | 0.1 | g |
| Water to | 1 | liter |
| pH to stated value with 4M NaOH | | |

Direct-positive magenta images of the sensitometric step-wedge were obtained, and the diffuse reflection densities to green light were measured. Results are given in Table III.

TABLE III

| Nucleator of Example No. | Nucleator Concentration | Activator pH 10.5 | | Activator pH 11.0 | |
|---|---|---|---|---|---|
| | | $D_{max}$ | $D_{min}$ | $D_{max}$ | $D_{min}$ |
| 4 | 22.5 mg/mol Ag | 0.84 | 0.37 | 1.50 | 0.62 |
| 4 | 45 mg/mol Ag | 0.97 | 0.46 | 1.72 | 0.85 |
| 1 | 90 mg/mol Ag | 0.59 | 0.33 | 1.06 | 0.59 |

EXAMPLE 8

Coatings were prepared broadly as described in Example 7, with the structure shown below.

| |
|---|
| 1.0 g/m² gelatin |
| silver, 0.65 gm²; gelatin, 1.08 g/m² |
| redox dye releaser, 0.54 g/m²; gelatin, 1.08 g/m² |
| Support |

Before coating the nucleator of Example 5 was added to the emulsion layer in the amount specified in Table IV.

The coatings were exposed and processed as in Example 7, using activator solutions of the following composition:

| | | |
|---|---|---|
| pH 11.0: | | |
| NaHCO₃ | 25 | g |
| Benzyl alcohol | 10 | ml |
| Ethanolamine | 5 | ml |
| 5-Methylbenzotriazole | 0.2 | g |
| Water to | 1 | liter |
| 4M NaOH to pH 11.0 | | |
| pH 11.5, 12.0: | | |
| Na₂HPO₄ | 36 | g |
| Benzyl alcohol | 10 | ml |
| Lysine hydrochloride | 5 | g |
| 11-Aminoundecanoic acid | 2 | g |
| 5-Methylbenzotriazole | 0.2 | g |
| Water to | 1 | liter |
| 4M NaOH to pH 11.5 or 12.0 | | |

Direct-positive magenta images-on-white of the sensitometric step-wedge were obtained, of similar photographic speed for each coating. Diffuse reflection densities to green light were measured, and results are given in Table IV.

TABLE IV

| Nucleator of Example No. | Nucleator Concentration | Activator pH 11.0 | | Activator pH 11.5 | | Activator pH 12.0 | |
|---|---|---|---|---|---|---|---|
| | | $D_{max}$ | $D_{min}$ | $D_{max}$ | $D_{min}$ | $D_{max}$ | $D_{min}$ |
| 5 | 4 mg/mole Ag | 0.40 | 0.16 | 1.43 | 0.21 | 1.87 | 0.27 |

EXAMPLE 9

N-[4-(2-Formylhydrazino)phenethyl]benzotriazole-4-sulphonamide

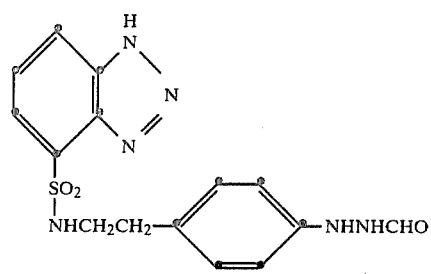

Benzotriazole-4-sulphonic acid

This was prepared by the method of Randell and Cox (British Patent Specification No. 1209919), in 81 percent yield.

Benzotriazol-4-sulphonyl chloride

Benzotriazole-4-sulphonic acid (5 g, 23 mM) was added, in portions, to chlorosulphonic acid (50 ml), whilst keeping the temperature of the acid below 0°. The resulting solution was heated at 120° overnight, cooled and carefully poured onto ice (1000 g). The solid which formed was collected by filtration, washed well with water and dried in vacuo. This material was dissolved in boiling ethyl acetate and decolorized using a small quantity of charcoal. The product crystallized from the ethyl acetate solution after petroleum ether (40° to 60°) was added, as a white solid (3.94 g, 72 percent), m.p. 173° to 175° (uncorr).

The preparation of Compound 2 directly from 5-methylbenzotriazole may be achieved by treatment with chlorosulphonic acid at 120° overnight. The yields of Compound 2 obtainable by this method are usually a little lower than those obtained from the two-stage synthesis outlined above.

N-(4-Nitrophenethyl)benzotriazole-4-sulphonamide

4-Nitrophenethylamine hydrobromide (27.17 g, 0.11 M) was dissolved in a mixture of tetrahydrofuran (25 ml), water (3 ml) and triethylamine (14.14 g, 19.6 ml, 0.14 M), and the solution was stirred at room temperature for one hour, after which time dimethylaniline (13.31 g, 0.11 M) was added.

A solution of benzotriazole-4-sulphonyl chloride (21.75 g, 0.1 M) in tetrahydrofuran (200 ml) was then added, dropwise, over half an hour. The reaction mixture was stirred at room temperature for 18 hours, poured into dilute hydrochloric acid (1N, 500 ml), and the oily mixture so formed was extracted with ethyl acetate (4×100 ml).

The extract was dried (sodium sulphate) and evaporated to leave a foam which crystallized from ethyl acetate/ether to afford the product (15 g, 43 percent), m.p. 155° to 156° (uncorr.).

N-(4-Aminophenethyl)benzotriazole-4-sulphonamide

N-(4-Nitrophenethyl)benzotriazole-4-sulphonamide (10 g, 29 mM) was suspended in ethanol (250 ml) and hydrogenated at 50 psi over 10 percent palladium on carbon catalyst (1 g) until hydrogen uptake ceased. The mixture was filtered through anhydrous sodium sulphate and the filtrate was concentrated under reduced pressure to leave the product as a pale yellow solid (6.53 g, 71 percent), m.p. 178° to 179° (uncorr.).

$C_{15}H_{15}N_5O_2S$ Requires: C, 53.0; H, 4.8; N, 22.1; S, 10.1. Found: C, 52.2; H, 4.9; N, 22.2; S, 9.9.

4-(Benzotriazole-4-sulphonamidoethyl)phenylhydrazinehydrochloride

N-(4-Aminophenethyl)benzotriazole-4-sulphonamide (4.53 g, 14 mM) was dissolved in a minimum of boiling ethanol (100 ml). The solution was cooled to −5°, saturated with dry hydrogen chloride and, after further cooling to −10°, amyl nitrite (1.84 g, 16 mM, 2.11 ml) was added over 10 minutes. The mixture was then stirred for 2 hours at −10°. The very small quantity of solid which remained was removed from the reaction mixture by filtration and the filtrate was added, all at once, to a solution of anhydrous stannous chloride (8.13 g, 43 mM) in ethanolic hydrogen chloride (10 ml) at 0°. The reaction mixture was stirred at 0° for 1 hour, left at 5° overnight and then poured into ether (1 liter). The solid which precipitated was collected (4.1 g).

This was dissolved in methanol (100 ml) and hydrogen sulphide was bubbled through the solution for 5 minutes. The inorganic solids were filtered off, and the filtrate was poured into ether (1.2 liters). The mixture was set aside at 5° overnight and the product which precipitated as a white hygroscopic solid (4 g, 76 percent) was collected. The mass spectrum of the product showed a peak of m/e 332 (M-HCl)·+ with measured mass 332.1065, $C_{14}H_{16}N_6O_2S$ requires 332.1055.

N-(4-(2-Formylhydrazino)phenethyl)benzotriazole-4-sulphonamide 4-(Benzotriazole-4-sulphonamidoethyl)phenylhydrazine hydrochloride (100 mg, 0.3 mM), sodium formate (37 mg, 0.5 mM) and formic acid (0.5 ml) were heated under reflux for 1 hour in ethyl formate (10 ml). The solvent was removed under reduced pressure and the residue was diluted with methanol. This solution was dried (sodium sulphate) and evaporated to leave an oil, which solidified when treated with tetrahydrofuran/dichloromethane to give the product (35 mg, 36 percent). This analyzed to N-[4-(2-Formylhydrazino)phenethyl]-benzotriazole-4-sulphonamide plus one mole of ethyl formate.

$C_{15}H_{16}N_6O_3S + 1$ mole ethyl formate Requires: C, 49.8; H, 5.1; N, 19.3; S, 7.4. Found: C, 49.4; H, 4.9; N, 19.5; S, 7.3.

The invention has been described in detail with particular reference to preferred embodiments thereof, but it will be understood that variations and modifications can be effected within the spirit and scope of the invention.

What is claimed is:

1. A silver halide emulsion comprised of silver halide grains capable of forming an internal latent image and, adsorbed to the surface of said silver halide grains, a nucleating amount of a triazole-substituted phenylhydrazide, wherein the phenyl moiety is triazole-substituted.

2. A silver halide emulsion according to claim 1 wherein said triazole-substituted phenylhydrazide is of the formula

wherein
R is an acyl group,
φ is a phenylene or substituted phenylene group, and
A is a moiety comprised of a triazole nucleus capable of promoting adsorption of the hydrazide to a silver halide grain surface.

3. A silver halide emulsion according to claim 1 wherein said triazole-substituted phenylhydrazide is of the formula

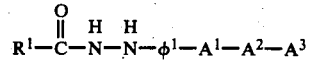

wherein
$R^1$ is hydrogen, an alkyl, cycloalkyl, haloalkyl, alkoxyalkyl or phenylalkyl substituent or a phenyl nucleus having a Hammett sigma-value-derived electron withdrawing characteristic more positive than −0.3,
$\phi^1$ is a m- or p-phenylene or an alkyl-, halo-, benzoxy- or alkoxy-substituted m- or p-phenylene group,
$A^1$ is alkylene or oxyalkylene,

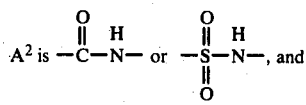

$A^3$ is a triazolyl or benzotriazolyl nucleus;

the alkyl and alkylene moieties in each instance having from 1 to 6 carbon atoms.

4. A silver halide emulsion according to claims 1, 2 or 3 wherein said triazole-substituted phenylhydrazide is present in a concentration of from 0.5 to 500 mg per mole of silver.

5. A silver halide emulsion according to claims 1, 2 or 3 wherein said silver halide grains are predominantly silver bromide and contain metal dopants occluded therein, which grains have been chemically sensitized on the surface thereof to a level which would produce a density of less than 0.4 when imagewise exposed and developed in a test surface developer for 5 minutes at 27° C. and to at least a level which would produce a density of greater than 0.5 in an undoped silver halide emulsion of the same grain size and halide composition when exposed and developed in the test surface developer, provided said emulsions are coated at a coverage of between about 3 and 4 grams per square meter.

6. A photographic element comprised of a support and, coated on said support, a silver halide emulsion layer comprising silver halide grains capable of forming an internal latent image and, absorbed to the surface of said silver halide grains, a nucleating amount of a triazole-substituted phenylhydrazide, wherein the phenyl moiety is trizole-substituted.

7. A photographic element according to claim 6 wherein said triazole-substituted phenylhydrazide is of the formula $$R-\overset{H}{N}-\overset{H}{N}-\phi-A$$

wherein
R is an acyl group,
φ is a phenylene or substituted phenylene group, and
A is a moiety comprised of a triazole nucleus capable of promoting absorption to a silver halide grain surface.

8. A photographic element according to claim 7 wherein said triazole-substituted phenylhydrazide is of the formula $$R^1-\overset{O}{\underset{}{C}}-\overset{H}{N}-\overset{H}{N}-\phi^1-A^1-A^2-A^3$$

wherein
$R^1$ is hydrogen, an alkyl, cycloalkyl, haloalkyl, alkoxyalkyl or phenylalkyl substituent or a phenyl nucleus having a Hammett sigma-value-derived electron withdrawing characteristic more positive than −0.3,
$\phi^1$ is a m- or p-phenylene or an alkyl-, halo-, benzoxy- or alkoxy-substituted m- or p-phenylene group,
$A^1$ is alkylene or oxyalkylene, $$A^2 \text{ is } -\overset{O}{\underset{}{C}}-\overset{H}{N}- \text{ or } -\overset{O}{\underset{O}{S}}-\overset{H}{N}-, \text{ and}$$

$A^3$ is a triazolyl or benzotriazolyl nucleus;
the alkyl and alkylene moieties in each instance having from 1 to 6 carbon atoms.

9. A photographic element according to claims 6, 7 or 8 wherein said triazole-substituted phenylhydrazide is present in a concentration of from 1.0 to 100 mg per mole of silver.

10. A photographic element according to claims 6, 7 or 8 wherein said silver halide grains contain a metal dopant; provide a maximum optical density less than 0.25 when coated on a support at a density of from 3 to 4 grams per square meter, exposed to a light intensity scale for a fixed time of from $1 \times 10^{-2}$ to 1 second and developed for 5 minutes at 25° C. in the surface developer; and provide a maximum optical density at least 5 times greater than the above maximum density when the above procedure is repeated additionally including in the surface developer 0.5 gram per liter of potassium iodide to form an internal developer.

11. A process of obtaining a direct-positive image comprising
imagewise exposing a photographic element comprised of a support and coated on the support a silver halide emulsion layer comprising silver halide grains capable of forming an internal latent image and, adsorbed to the surface of the silver halide grains, a nucleating amount of a traizole-substituted phenylhydrazide, wherein the phenyl moiety is traizole-substituted, and
selectively developing the silver halide grains remaining unexposed.

12. In an image transfer film unit which comprises
a photographic element comprising a support and coated thereon at least one silver halide emulsion layer containing radiation-sensitive internal latent image-forming silver halide grains and, adsorbed to the surface of said silver halide grains, a nucleating agent, said photographic element including an image dye-providing material within or in contact with said silver halide emulsion layer,
an image-receiving means positioned to receive image dye from said photographic element,
an alkaline processing composition,
means containing and adapted to release said alkaline processing composition for contact with said emulsion layer, and
a silver halide developing agent located in at least one of the photographic element and the alkaline processing composition,
the improvement wherein said nucleating agent is a triazole-substituted phenylhydrazide of the formula $$R-\overset{H}{N}-\overset{H}{N}-\phi-A$$

wherein
R is an acyl group,
φ is a phenylene or substituted phenylene group, and
A is a moiety comprised of a triazole nucleus capable of promoting adsorption to a silver halide grain surface.

13. An improved image transfer film unit according to claim 12 wherein said film unit incorporates an antifoggant.

14. An improved image transfer film unit according to claim 13 wherein said antifoggant is a benzotriazole antifoggant.

15. An improved image transfer film unit according to claim 12 wherein said triazole-substituted phenylhydrazide is of the formula

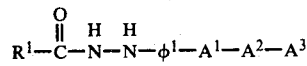

wherein
$R^1$ is hydrogen, an alkyl, cycloalkyl, haloalkyl, alkoxyalkyl or phenylalkyl substituent or a phenyl nucleus having a Hammett sigma-value-derived electron withdrawing characteristic more positive than $-0.3$, $\phi^1$ is m- or p-phenylene or an alkyl-, halo-, benzoxy- or alkoxy-substituted m- or p-phenylene group, $A^1$ is alkylene or oxyalkylene,

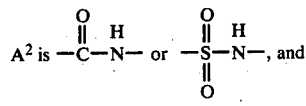

$A^3$ is a triazolyl or benzotriazolyl nucleus;
the alkyl and alkylene moieties in each instance including from 1 to 6 carbon atoms.

16. An image transfer film unit comprising (a) a photographic element comprising a support bearing
(1) a layer containing a blue-sensitive silver halide emulsion having in contact therewith an immobile material capable of releasing a mobile yellow image dye,
(2) a layer containing a green-sensitized silver halide emulsion having in contact therewith an immobile material capable of releasing a mobile magenta image dye, and
(3) a layer containing a red-sensitized silver halide emulsion having in contact therewith an immobile material capable of releasing a mobile cyan image dye, wherein each of said silver halide emulsions comprises silver halide grains having metal dopants occluded therein, said grains being substantially unfogged on their surfaces and being chemically sensitized on their surfaces (a) to a level which will provide a maximum density of less than 0.4 when developed in a test surface developer of the composition indicated below for 5 minutes at 27° C. after exposure to a light intensity scale for a fixed time of from $1 \times 10^{-2}$ to 1 second when said photosensitive composition is coated at a coverage of between about 3 and 4 grams of silver per square meter, and (b) to at least a level which would provide a maximum density of at least 0.5 using undoped silver halide grains of the same grain size and halide composition when coated, exposed and developed in like manner,
(b) an image-receiving means positioned to receive image dye from said photographic element,
(c) an aqueous alkaline processing composition,
(d) means containing and adapted to release said alkaline processing composition into contact with said silver halide emulsions,
(e) a silver halide surface developing agent located in said processing composition, and
(f) from 1 to 100 mg per mole of silver of a nucleating agent adsorbed to said silver halide grains within at least one of said silver halide emulsion layer, said nucleating agent having the formula

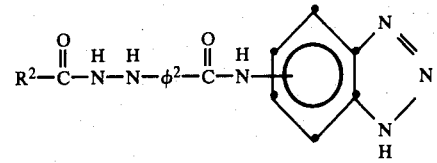

wherein
$R^2$ is hydrogen or methyl,

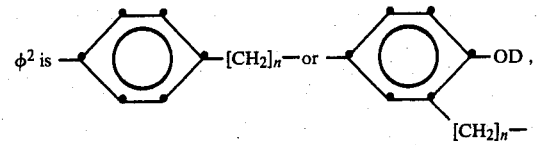

n is an integer of from 1 to 4, and
D is alkyl of from 1 to 4 carbon atoms;
the test surface developer consisting essentially of

| | | |
|---|---|---|
| Water (52° C.) | 500.00 | cc |
| N-methyl-p-aminophenol sulfate | 2.5 | g |
| Sodium sulfite, desiccated | 30.0 | g |
| Hydroquinone | 2.5 | g |
| Sodium metaborate | 10.0 | g |
| Potassium bromide | 0.5 | g |
| Water to make | 1 | liter. |

17. A process of producing a transferred photographic dye image comprising
imagewise exposing a photographic element comprised of a support and, coated on the support, a silver halide emulsion layer comprising silver halide grains capable of forming an internal latent image and, adsorbed to the surface of the silver halide grains, a nucleating amount of a triazole-substituted phenylhydrazide of the formula

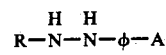

wherein
R is an acyl group,
$\phi$ is a phenylene or substituted phenylene group, and
A is a moiety comprised of a triazole nucleus capable of promoting adsorption to the surfaces of the silver halide grains, said photographic element including an image dye-providing material which exhibits an alteration in mobility as a function of silver halide development within or in contact with said silver halide emulsion layer,
selectively developing the silver halide grains remaining unexposed, and
transferring mobile dye to a receiver to form a transferred dye image.

* * * * *

UNITED STATES PATENT AND TRADEMARK OFFICE
CERTIFICATE OF CORRECTION

PATENT NO. : 4,278,748

DATED : July 14, 1981

INVENTOR(S) : Jasbir Sidhu, Michael J. Simons and Miroslav V. Mijovic

It is certified that error appears in the above-identified patent and that said Letters Patent are hereby corrected as shown below:

Title Page, add as coinventor ---Brian D. Baigrie,

New Denham, --.

Signed and Sealed this

Seventeenth Day of August 1982

[SEAL]

Attest:

GERALD J. MOSSINGHOFF

Attesting Officer — Commissioner of Patents and Trademarks